United States Patent [19]
Miyazaki et al.

[11] Patent Number: 6,068,595
[45] Date of Patent: May 30, 2000

[54] CONTROL OF SETTING PHASE-ENCODING DIRECTION IN MRI

[75] Inventors: Mitsue Miyazaki, Otawara; Nobuyasu Ichinose, Nasu-Gun, both of Japan

[73] Assignee: Kabushiki Kaisha Toshiba, Kawasaki, Japan

[21] Appl. No.: 08/942,683

[22] Filed: Oct. 2, 1997

[30] Foreign Application Priority Data

May 26, 1997 [JP] Japan ................................ 9-149886

[51] Int. Cl.[7] ........................................... A61B 5/055
[52] U.S. Cl. ........................ 600/410; 324/309; 600/428
[58] Field of Search .................................. 600/410, 425, 600/428; 324/307, 309; 382/128

[56] References Cited

PUBLICATIONS

Constable et al, "The Loss of Small Objects in Variable TE Imaging: Implications for FSE, RARE, and EPI", Magnetic Resonance in Medicine 28, pp. 9–24 (1992).
Hinks et al, "Gradient Moment Nulling in Fast Spin Echo", MRM 32: 698–706 (1994).

*Primary Examiner*—Marvin M. Lateef
*Assistant Examiner*—Eleni Mantis Mercader
*Attorney, Agent, or Firm*—Nixon & Vanderhye P.C.

[57] ABSTRACT

By employing controlled setting of a phase-encoding direction in MRI, for imaging a tissue or blood flow composed of spins whose time $T_2$ is rather short or ranges from 100 to 200 milliseconds, signal levels induced by the blood flow or the like are raised in order to maintain a good signal-to-noise ratio. An image enjoying an excellent depiction ability can be produced without the loss of information of directivities of blood flows or tissues running in diverse directions. An MRI system utilizing the Fourier transform comprises an element for scanning the same region to be imaged of a subject a plurality of times while changing phase-encoding directions, and an element for producing image data of one frame on the basis of MR rawdata of a plurality of frames. The producing element includes, for example, a unit for reconstructing image data in the real space by processing frame by frame MR raw data of a plurality of frames, and a unit for synthesizing reconstructed image data of the plurality of frames so as to produce image data of one frame. Synthesis is, for example, addition or maximum intensity projection.

35 Claims, 21 Drawing Sheets

CONTROL OF SETTING PHASE-ENCODING DIRECTION IN MRI

BACKGROUND OF THE INVENTION

1. Field of the Invention

The present invention relates to magnetic resonance imaging for imaging the inside of a subject on the basis of a magnetic resonance phenomenon occurring in the subject. More particularly, this invention is concerned with a magnetic resonance imaging (MRI) system and magnetic resonance (MR) imaging method suitable for imaging of a tissue or blood flow in a subject composed of nuclear spins whose transverse (spin-spin) relaxation time ($T_2$) is rather short.

2. Description of the Related Art

Magnetic resonance imaging is a technique for magnetically exciting nuclear spins in a subject positioned in a static magnetic field by applying a radio-frequency signal with the Larmor frequency, and reconstructing an image using an MR signal induced with the excitation or providing a spectrum of an MR signal.

For imaging the vessels in the lungs or the vessels in the liver (portal vein) according to magnetic resonance imaging, various requirements must be satisfied. One of the requirements is to improve a signal-to-noise ratio by raising signal levels representing a vascular image. Another one is to minimize artifacts caused by body motions.

As a technique coping with the former or a technique for raising a signal, there is a technique of averaging n (larger than 1) MR data items pixel by pixel. For carrying out averaging, the number of shots or the number of scans is increased in order to increase the number of data items per pixel. Thus, the frequency of accumulation per pixel is increased. A phase-encoding direction, that is, a direction in which the distribution of spins is phase-encoded in order to acquire an MR signal used for averaging is set to a certain direction.

Moreover, for satisfying the latter requirement, that is, for suppressing occurrence of body-motion artifacts, there is an approach in which a patient is asked to hold his or her breath. This makes it possible to minimize body-motion artifacts caused by the motion of the lungs.

However, when a person's breath is held a plurality of times and MR data items acquired during periods of breath hold are used to produce an image, the image may be blurred due to the influence of body-motion artifacts caused by the movement of the patient's body. For this reason, a patient is usually asked to hold his or her breath only once. Efforts are made to increase the frequency of accumulation required for averaging during the one breath hold.

However, especially when fast spin echo imaging (FSE) or echo planar imaging (EPI) is adopted, even if the approach to one breath hold and the averaging technique are adopted, the running state of components whose time $T_2$ is rather short (or ranges from 100 to 200 msec) (a blood flow, or especially, a vessel in the lungs or a vessel in the liver (portal vein) or a vas) cannot be visualized successfully. This combination is therefore unsatisfactory in terms of visualization ability.

This is attributable to the fact that the half-width of a function of an MR signal induced by components whose time $T_2$ is rather short (hereinafter, simply, a blood flow) in relation to pixel locations in a phase-encoding direction is large (stretched), and a whole image is blurred in the phase-encoding direction.

When an image is blurred in the phase-encoding direction, pixel values expressing an image of a blood flow crossing (orthogonal to) the phase-encoding direction and those expressing surrounding tissues are added up and averaged. This results in deteriorated resolution. In other words, in an image, it becomes hard to discriminate a blood flow running in a direction crossing the phase-encoding direction from surrounding tissues.

When MR data acquired with a phase-encoding direction set to a given direction is subjected to averaging, the resolution of a blood flow running in the phase-encoding direction improves. However, the resolution of a blood flow running in any other direction remains low because the values of blurred pixels are merely averaged.

In the case of known averaging, it is hard to produce an image depicting vertically-and-laterally-running blood flows with the running directions of the blood flows clearly discernible without the loss of running information. Blood flows running in directions other than a phase-encoding direction are likely to be missing out of an image, and can sometimes not be identified by looking carefully at the image. This problem is serious in imaging of a blood flow composed of spins whose time $T_2$ is rather short.

SUMMARY OF THE INVENTION

The present invention attempts to break through the foregoing current situation of known art. Specifically, an object of the present invention is to provide an MRI system and MR imaging method that when blood flows or the like are imaged, can produce an image enjoying an excellent depiction ability without the loss of information of directivities exhibited by blood flows or tissues running in diverse directions while maintaining a good signal-to-noise ratio by raising signal levels induced by the blood flows.

Another object of the present invention is to produce an image enjoying an excellent depiction ability without the loss of information of directivities exhibited by blood flows or tissues running in diverse directions while maintaining a good signal-to-noise ratio by raising signal levels induced by the blood flows each composed of spins whose time $T_2$ is rather short or ranges from 100 to 200 milliseconds.

Another object of the present invention is to adopt an approach to breath hold in combination with the technique of changing the phase-encoding direction.

Another object of the present invention is to adopt an ECG gating technique in combination with the technique of changing the phase-encoding direction and/or the breath hold.

For accomplishing the above objects, one aspect of the present invention relates to an MRI system for producing images of a subject using a Fourier transform. The MRI system comprises a scanning means for acquiring MR raw data of a plurality of sets by scanning the same region to be imaged of the subject a plurality of times while changing phase encoding directions, and a producing means for producing image data of one set on the basis of the MR raw data of a plurality of sets.

As another aspect of the invention, there is a method of MR imaging producing images of a subject employing a Fourier transform of MR raw data acquired from the subject by magnetic scan under a state that pulsed gradients are applied to the subject in phase-encoding, read-out, and slice directions set to the subject, comprising the steps of: scanning the same region to be imaged of the subject a plurality of times with the phase-encoding direction changed for each scan, thus acquiring the MR raw data of a plurality of sets corresponding to the plurality of scans; reconstructing the MR raw data of each of the plurality of sets into image data in a real space: and synthesizing the reconstructed image data of the plurality of sets.

According to the MRI system and MR imaging method of the present invention, when blood flows or the like are imaged by adopting the averaging technique, signal levels induced by the blood flows can be raised in order to maintain a good signal-to-noise ratio. An image enjoying an excellent depiction ability can be produced without the loss of information of directivities of blood flows running in diverse directions. In particular, when a blood flow or tissue composed of spins whose time $T_2$ is rather short or ranges from 100 to 200 milliseconds is imaged, the advantages of the present invention are markedly noticeable. Moreover, the imaging method of the present invention can be implemented in combination with an approach using one breath hold. The physical and mental loads incurred by a patient are therefore limited. Thus, a high-quality MR image with few body-motion artifacts capable of contributing to improvement of diagnostic performance can be produced.

The remaining features of the invention will be clearly understood from the description of various preferred embodiments, which are described with accompanying drawings below.

DESCRIPTION OF THE PREFERRED EMBODIMENTS

Figure 1:
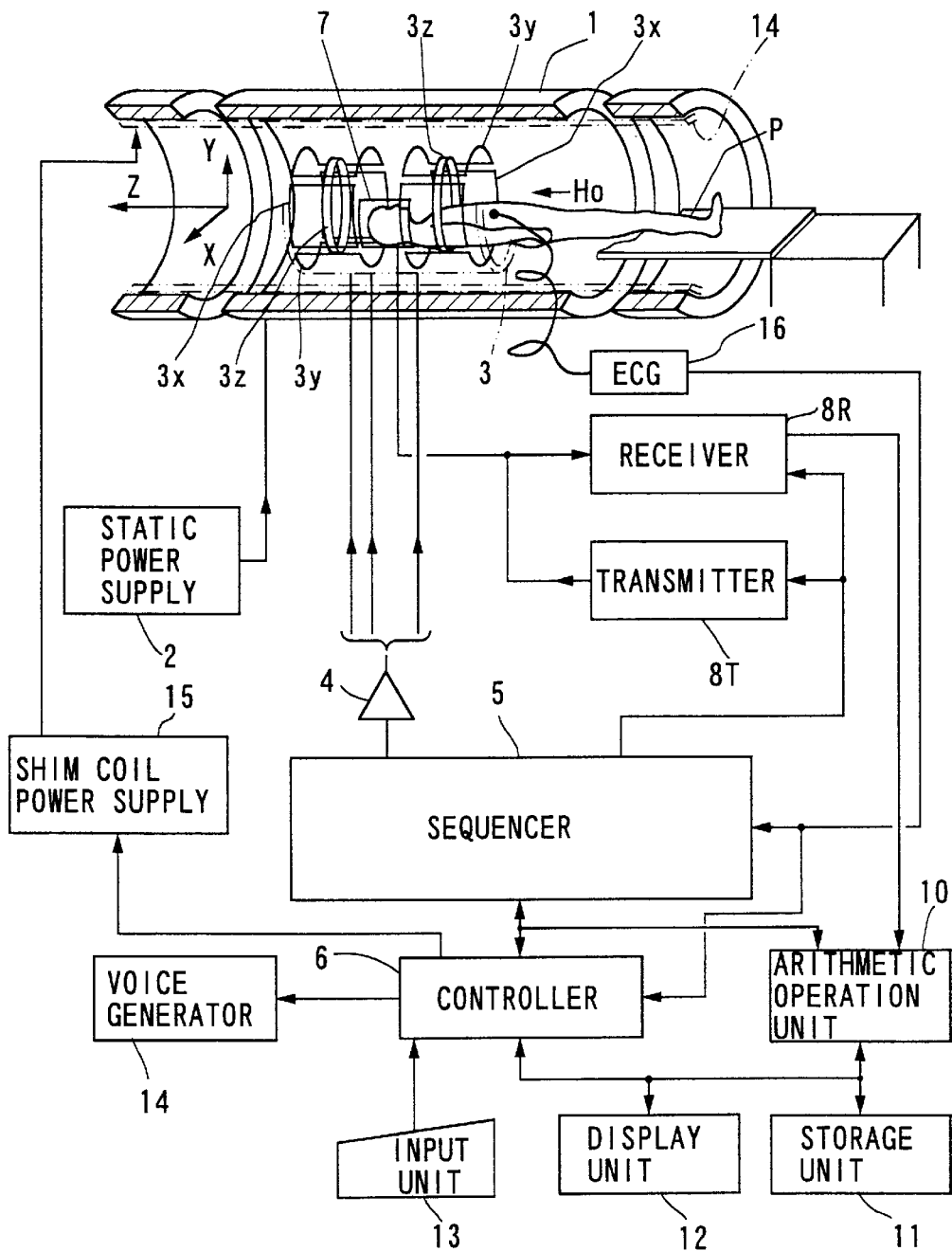
FIG. 1 is a block diagram showing an example of an MRI system in accordance with the embodiments of the present invention.

FIG. 1 shows the outline configuration of a magnetic resonance imaging (MRI) system in accordance with the embodiments of the present invention.

The MRI system comprises a patient couch on which a patient P lies down, static magnetic field generating components for generating a static magnetic field, magnetic field gradient generating components for appending positional information to a static magnetic field, transmitting receiving components for transmitting and receiving a radio-frequency signal, control and arithmetic operation components responsible for control of the whole system and for image reconstruction, and an electrocardiographing component for acquiring an ECG signal of a patient.

The static magnetic field generating components includes a magnet 1 that is of, for example, a superconducting type, and a static power supply 2 for supplying a current to the magnet 1, and generates a static magnetic field $H_0$ in an axial direction (Z-axis direction) in a cylindrical bore (diagnostic space) into which the patient P is inserted. The magnet unit includes shim coils 14. A current used to homogenize a static magnetic field is supplied from a shim coil power supply 15 to the shim coils 14 under the control of a controller to be described later. The couch top of the patient couch on which the patient P lies down can be inserted into the bore of the magnet 1 so that the couch top can be withdrawn.

The magnetic field gradient generating components includes a gradient coil unit 3 incorporated in the magnet 1. The gradient coil unit 3 includes three pairs (kinds) of x, y, and z coils 3x to 3z used to generate magnetic field gradients changing in strength in X-axis, Y-axis, and Z-axis directions that are mutually orthogonal. The magnetic field gradient generator further includes a gradient power supply 4 for supplying a current to the x, y, and z coils 3x to 2z. The gradient power supply 4 supplies a pulsating current used to generate a magnetic field gradient to the x, y, and z coils 3x to 3z under the control of a sequencer 5 that will be described later.

The pulsating current supplied from the gradient power supply 4 to the x, y, and z coils 3x to 3z is controlled, whereby magnetic field gradients changing in the three axial directions, that is, the X, Y, and Z directions are synthesized. Thus, directions in which a slice selective magnetic field gradient $G_S$, a phase-encoding magnetic field gradient $G_E$, and a readout (frequency-encoding) magnetic field gradient $G_R$ are applied can be specified and changed arbitrarily. The magnetic field gradients to be applied in a slice direction, a phase-encoding direction that is a direction the distribution of spins in which is phase-encoded, and a readout direction that is a direction in which an MR signal is read are superposed on the static magnetic field $H_0$.

The transmitting/receiving components include a radio-frequency coil 7 located in the vicinity of the patient P in the scanning space inside the magnet 1, and a transmitter 8T and receiver 8R connected to the coil 7. The transmitter 8T and receiver 8R supply radio-frequency pulses with the Larmor frequency, which are used to excite nuclear magnetic resonance (NMR), under the control of the sequencer 5 to be described later, receive an MR signal (radio-frequency signal) via the radio-frequency coil 7, carries out various kinds of signal processing, and then produces a corresponding digital signal.

Figure 2:
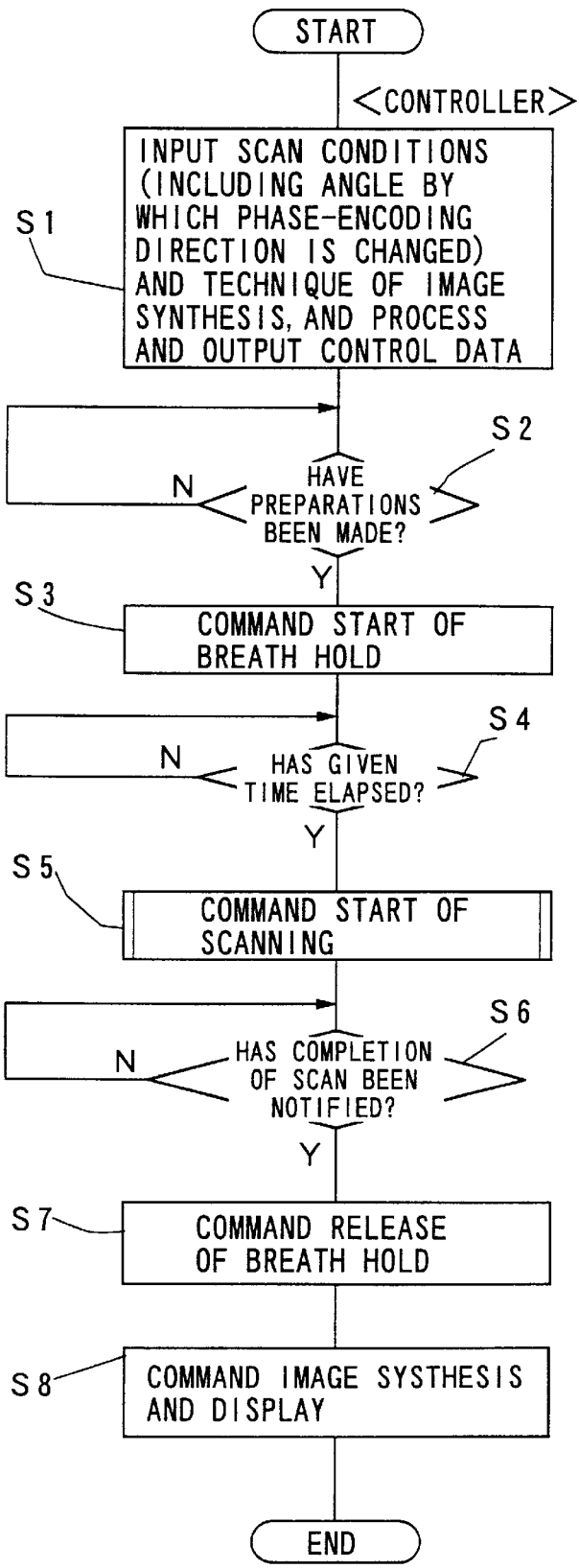
FIG. 2 is a flowchart outlining an example of an imaging procedure to be executed by a controller in a first embodiment.

Furthermore, the control and arithmetic operation components include the sequencer 5, a controller 6, an arithmetic operation unit 10, a storage unit 11, a display unit 12, an input unit 13, and a voice generator 14. Among them, the controller 6 includes a computer. The controller 6 has the function of following a procedure that is a software program stored in the computer so as to command the sequencer 5 to provide pulse-sequence information, matching in timing the operations of the control blocks including the sequencer 5 in the whole system, and managing the control blocks on a centralized basis. FIG. 2 that will be referred to later shows an example of scan control processing.

The sequencer 5 has a CPU and memory, stores pulse-sequence information sent from the controller 6, and controls a series of operations to be performed by the gradient power supply 4, transmitter 8R, and receiver 8T according to the stored information. What is referred to as pulse-sequence information is all information required for operating the gradient power supply 4, transmitter 8R, and receiver 8T according to a pulse sequence. For example, pulse-sequence information includes information concerning the strength of a pulsating current to be applied to the x, y, and z coils 3x to 3z, and the application time and timing thereof.

As for the pulse sequence, a pulse sequence used for either two-dimensional (2D) scanning or three-dimensional (3D) scanning will do as long as the Fourier transform can be applied for image reconstruction.

Moreover, the pulse sequence may be a pulse train to be applied according to any of MR imaging techniques; spin echo (SE) imaging, field gradient (FE) echo imaging, fast SE (FSE) imaging, echo planar imaging (EPI), and fast asymmetric SE (FASE) imaging.

The arithmetic operation unit 10 inputs digital data represented by an MR signal sent from the receiver 8R, maps raw data in Fourier space (or k-space or frequency space) formed in an incorporated memory, and performs a two-dimensional or three-dimensional Fourier transform on the raw data so as to reconstruct an image in real space. Moreover, the arithmetic operation unit 10 carries out synthesis of image data which is a constituent feature of the present invention. A preferred example of synthesis is addition in which reconstructed image data items of a plurality of frames are added up pixel by pixel or maximum intensity projection (MIP) in which a maximum pixel value is selected pixel by pixel from among reconstructed image data items of a plurality of frames. Addition includes simple addition, averaging, and weighting and addition. Another example of synthesis is such that axes associated with a plurality of frames in the Fourier space are matched with one another and raw data items are synthesized as they are in order to produce raw data of one frame.

The storage unit 11 can preserve not only raw data and reconstructed image data but also image data having undergone synthesis. The display unit 12 displays an image, and can be used to input desired information entered at the input unit 13 by an operator; such as, scan conditions, a pulse sequence, and a technique of image synthesis to the controller 6.

The voice generator 14 utters, for example, a voice message informing the start or end of breath hold in response to a command sent from the controller 10.

The electrocardiography component is made up of an ECG (electrocardiograph) unit 16 outputting an ECG signal of a patient P during scanning. The ECG signal is supplied to the controller 6 and sequencer 5 for ECG gated acquisition of MR raw data. When desired, the controller 6 and sequencer 5 can execute the ECG gated processing.

(First Embodiment)

Next, scan control operations in a first embodiment will be described with reference to FIGS. 2 to 8.

A patient P is positioned in the diagnostic space in the magnet 1. When the MRI system is activated, the controller 6 executes a given main program and carries out the processing described in FIG. 2 as part of the main program.

The processing will be described. At step S1 in FIG. 2, the controller 6 inputs scan conditions (for example, an image size, the number of scans, a standby time between scans, and a pulse sequence dependent on a region to be scanned) and information of a technique of image synthesis (synthesis of reconstructed images, synthesis in the frequency space, addition, or MIP. In the case of addition, simple addition, averaging, or weighting and addition), processes control information according to the input information, and outputs the control information to the sequencer 5 and arithmetic operation unit 10.

During the processing of step S1, the controller 6 automatically calculates an angle by which a phase-encoding direction is changed according to the number of scans required for image synthesis (that is, the number of images to be produced for the same region to be imaged), appends angle-change information, that is, information of the angle by which the phase-encoding direction for each scan is changed to a pulse sequence, and transmits the information to the sequencer 5. According to the angle-change information, when the number of images to be synthesized is, for example, two, after the first scan is completed, before the second scan is executed, the phase-encoding direction set for the first scan is changed by 90°.

If it is judged at step S2 that an instruction indicating the completion of pre-scan preparations has been issued, a command indicating the start of breath hold is output to the voice generator 14 at step S3. This causes the voice generator 14 to utter a voice message saying "Hold breathing." In response to this message, the patient holds breathing (See FIG. 4).

After commanding the start of breath hold, the controller 6 stands by as it is for a given time interval (for example, one second) at step 4, and thus adjusts timing to allow the patient to surely hold breathing.

Figure 3:
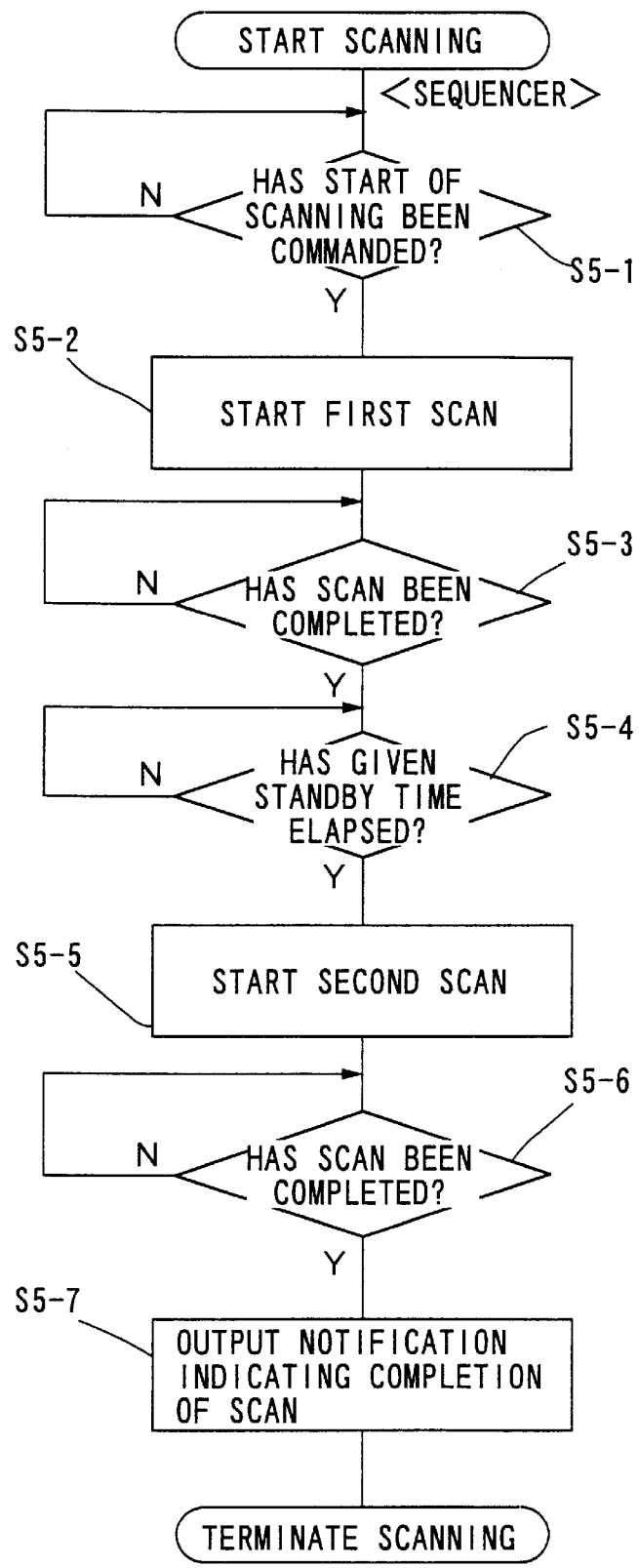
FIG. 3 is a flowchart outlining an example of scan control processing to be executed by a sequencer in the first embodiment.
Figure 4:
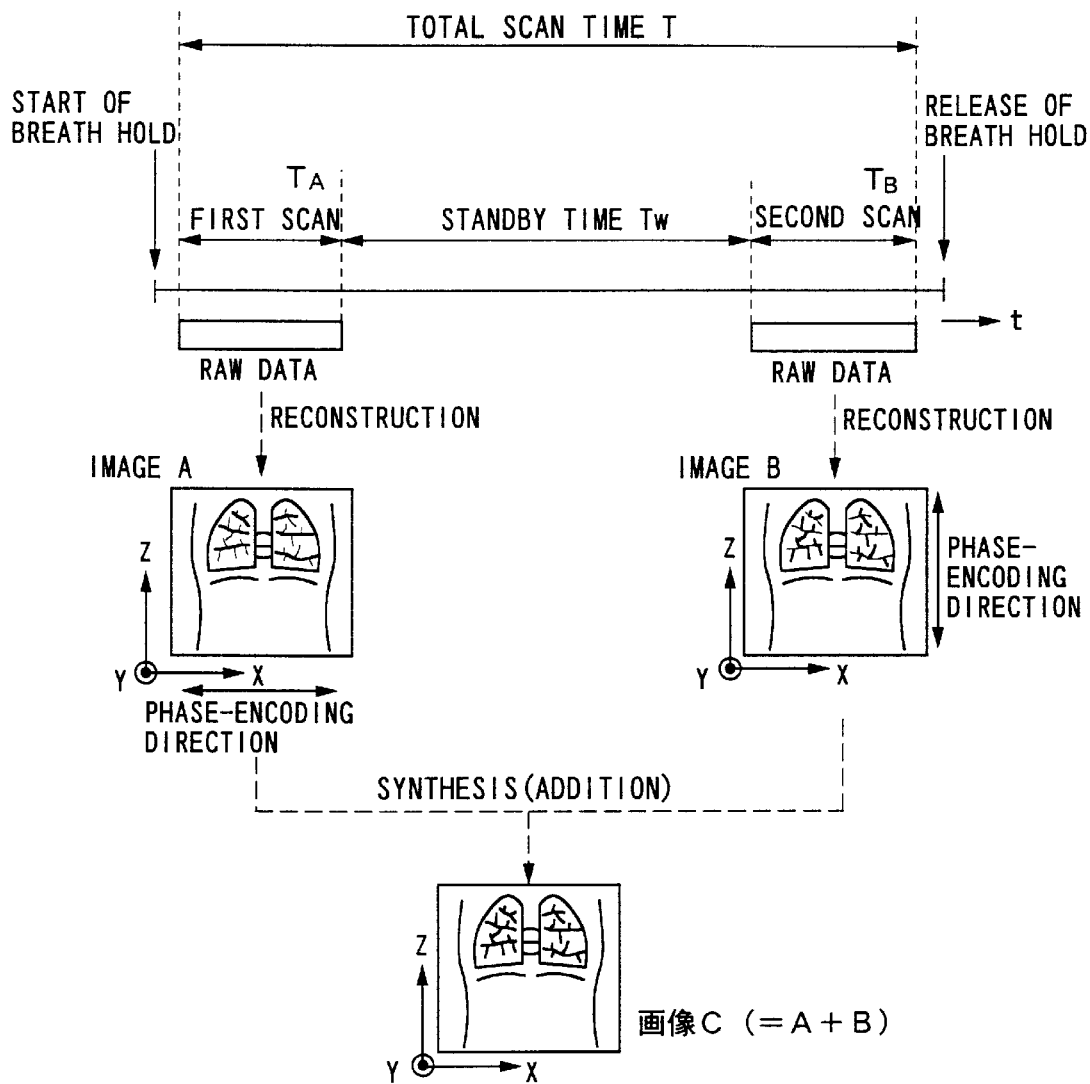
FIG. 4 is a diagram for illustratively explaining the relationship between a scanning sequence and image synthesis in the first embodiment.

When the given standby time elapses, the controller 6 passes control to step S5 and commands the sequencer 5 to start scanning. In response to the command, the sequencer 5 drives the transmitter 8T and gradient power supply 4 according to pulse-sequence information that has already been transmitted and stored, and executes scanning. FIG. 3 describes an example of the scanning and FIG. 4 shows the timing.

In the example of processing described in FIG. 3, the number of scans is two, and image synthesis to be described later is addition of two reconstructed images. The example of scan control processing will be described.

The sequencer 5 normally stands by while judging whether or not a scanning start command is sent from the controller 6 (step S5-1). When scanning is commanded, the sequencer 5 carries out the first scan on the basis of a commanded phase-encoding direction. For the first scan, for example, the FSE imaging is selected, the phase-encoding direction is set to the Z-axis direction, and the readout direction (frequency-encoding direction) is set to the X-axis direction (step S5-2. See FIG. 4). As a result, MR raw data (k-space data) of one frame resulting from scanning of, for example, the lungs is acquired.

Spin echoes produced in the patient P by carrying out the FSE imaging are received by the radio-frequency coil 7, and sent to the receiver 8R. The receiver 8R performs various kinds of pre-processing on the spin echoes. The spin echoes are thus converted into a digital quantity. Echo data that is the digital quantity is sent to the arithmetic operation unit 10 and mapped in, for example, a two-dimensional k-space in an incorporated memory. The echo data set in the k-space is subjected to, for example, a two-dimensional Fourier transform according to proper timing and thus converted into a tomographic image in the real space. The reconstructed image data is temporarily stored in the storage unit 11, and the second scan is awaited.

After commanding the first scan, the sequencer 5 stands by while judging whether or not the scan is completed (step S5-3).

Thereafter, the sequencer 5 stands by for a given time Tw until the second scan is started (step S5-4). The standby time Tw is intended to spend time until the behavior of nuclear spins excited during the first scan returns to the steady state attained before application of excitation pulses. Owing to the standby time, the behavior of nuclear spins to be excited during the second scan will hardly be affected by excitation occurring during the first scan. This results in more faithful echo data. The standby time Tw is, for example, in the order of 6 seconds. Incidentally, in one preferred mode of the present invention, an operator is allowed to adjust the length of the standby time Tw at the input unit 13.

When the standby time Tw elapses, the sequencer 5 carries out the second scan for the same plane to be scanned as that scanned during the first scan (step S5-5). However, the phase-encoding direction is changed by a pre-set angle. For example, the phase-encoding direction for the second scan is set to a direction deviated by 90° from the phase-encoding direction for the first scan. Assume that the phase-encoding direction is changed to the X-axis direction and the readout direction (frequency-encoding direction) is changed to the Z-axis direction. Under these conditions for encoding, the second scan is carried out (See FIG. 4). Processing to be performed on acquired spin echoes is the same as that carried out during the first scan.

When judging that the second scan is completed, the sequencer 5 notifies the sequencer 6 of the completion of the scan (steps S5-6 and S5-7).

At step S6 in FIG. 2, the controller 6 in the standby state receives the notification saying the completion of the scan from the sequencer 5. The controller 6 then passes control to step S7, and outputs a command of release of breath hold to the voice generator 14. The voice generator 14 then utters a voice message saying, for example, "You can breathe." toward the patient (See FIG. 4).

When the data acquisition processing is completed, the controller 6 commands the arithmetic operation unit 10 to synthesize and display reconstructed images A and B produced by the two scans and stored temporarily in the storage unit 11 (step S8). The technique of synthesis is recognized at step Si of inputting. Image synthesis is carried out according to the technique, whereby one synthetic image C is produced. As the technique of synthesis, in this case, addition in which two images A and B are added up pixel by pixel or maximum intensity projection in which a maximum pixel value is selected pixel by pixel from two images A and B can be adopted. In the case of addition, since any of simple addition, averaging, and weighting and addition is commanded, processing proceeds according to the commanded technique. As a results, as shown in FIG. 4, the synthetic image C of the two reconstructed images A and B is produced.

As mentioned above, according to this embodiment, a new synthetic image can be produced using a plurality of images represented by echo data acquired by changing phase-encoding directions. Owing to the angle control of a phase-encoding direction, the synthetic image is superb in the ability to depict blood flows each exhibiting a rather short time $T_2$. The reasons will be described.

Figure 5:
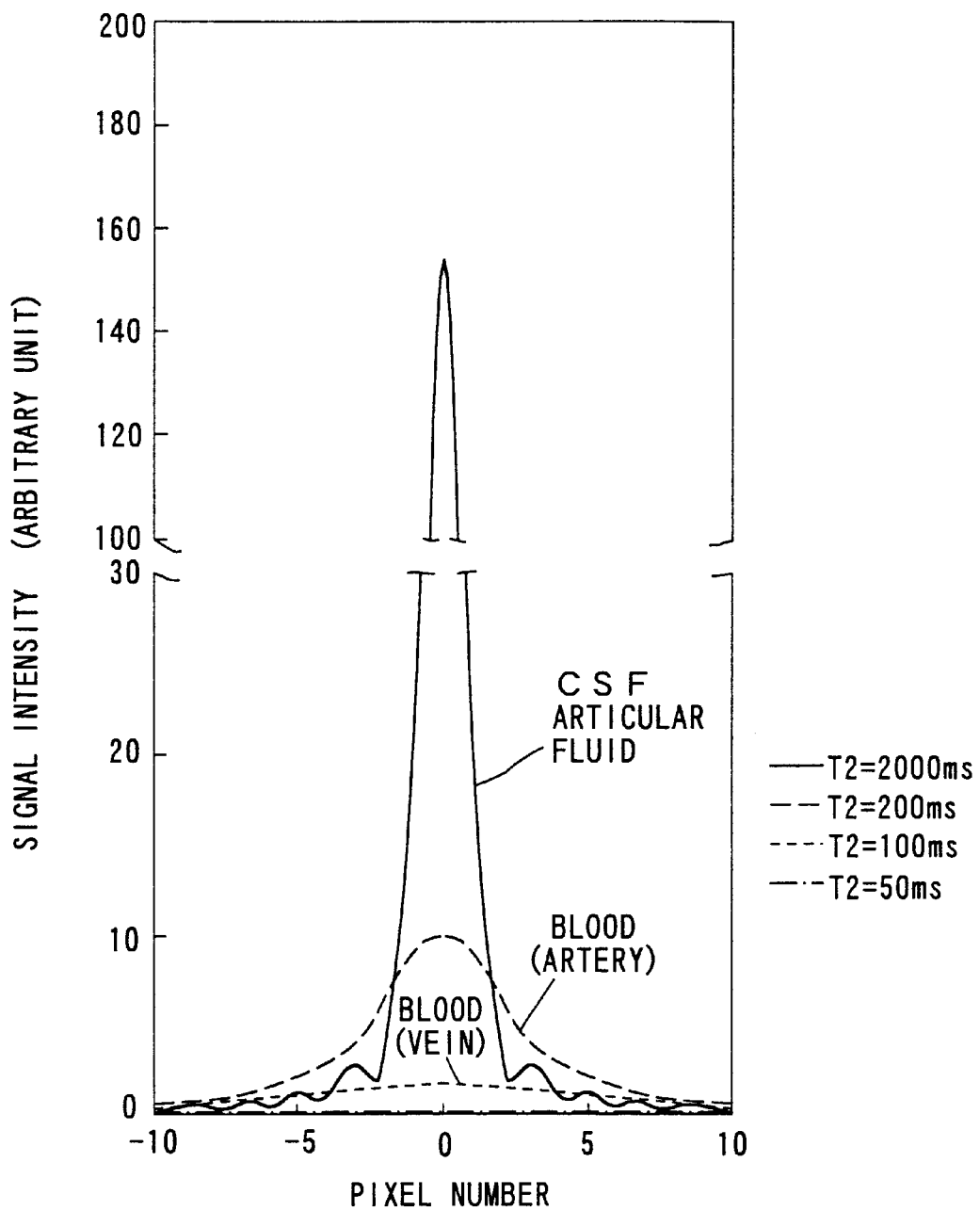
FIG. 5 is a graph for explaining the spread of signal levels along an axis of abscissae indicating a, phase-encoding direction.

In general, a blood flow typical of the pulmonary vessels and hepatic vessels (portal vein) is known to exhibit a rather short time $T_2$ (ranging from 100 to 200 milliseconds). It has been revealed that the half-width of a function of a signal induced by a blood flow exhibiting the rather short time $T_2$ is larger than that of a function of a signal induced by the cerebrospinal fluid (CSF) or articular fluid ($T_2$>2000 msec). This is described in, for example, the literature entitled "The loss of small objects in Variable TE imaging: Implications for FSE, RARE, and EPI" written by R. Todd Constable and John C. Gore (Magnetic Resonance in Medicine, Vol. 28, P.9–24, February of 1992). According to the literature, spreads of signal levels induced by materials exhibiting different times $T_2$ are, as shown in FIG. 5, expressed by "point spread functions." The graph of FIG. 5 plots the functions observed under the conditions that the static magnetic field strength is 1.5 T, the time TEeff is 240 milliseconds, and the inter-echo time spacing (ETS) is 12 milliseconds. The axis of abscissae indicates the number of pixels in a phase-encoding direction in an image, and the axis of ordinates indicates the signal intensity expressed in any unit. Compared with the function of the signal intensity induced by the CSF or articular fluid exhibiting a time $T_2$ of 200 milliseconds, the function of the signal intensity induced by blood (artery) exhibiting a time $T_2$ of 200 milliseconds has a larger half-width. This can be said to be apparently equivalent to the situation in which the width in phase-encoding direction of each pixel in the image of the blood (artery) exhibiting the time $T_2$ of 200 milliseconds is larger than that in the image of the CSF or articular fluid (each pixel in the image of the blood is stretched). This means that the whole image of the blood (artery) exhibiting the time $T_2$ of 200 milliseconds is blurred in the phase-encoding direction to a greater extent than that of the CSF or articular fluid.

The present invention actively utilizes the fact that the spread (blur) of signal levels induced by blood exhibiting a short time $T_2$ along the axis of abscissae indicating pixel locations in the phase-encoding direction is greater than that of signal levels induced by an entity exhibiting a long time $T_2$.

Figure 6A:
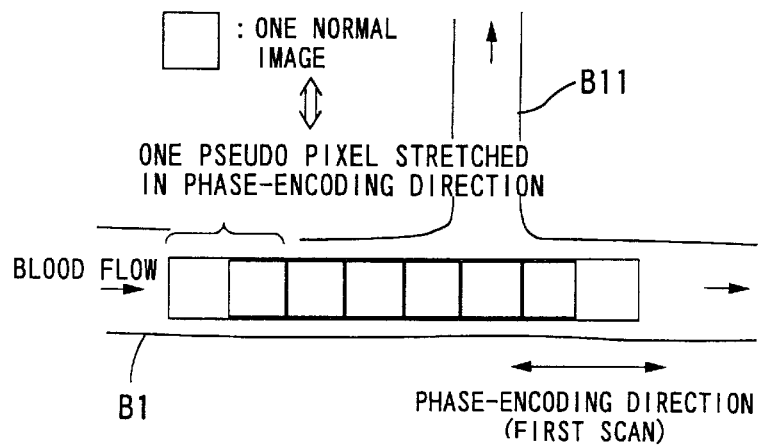
FIGS. 6A to 6C are diagrams illustratively showing examples of an image represented by signal levels that are plotted to spread along an axis of abscissae indicating a phase-encoding direction set for a single scan and an example of an image resulting from image synthesis.
Figure 6B:
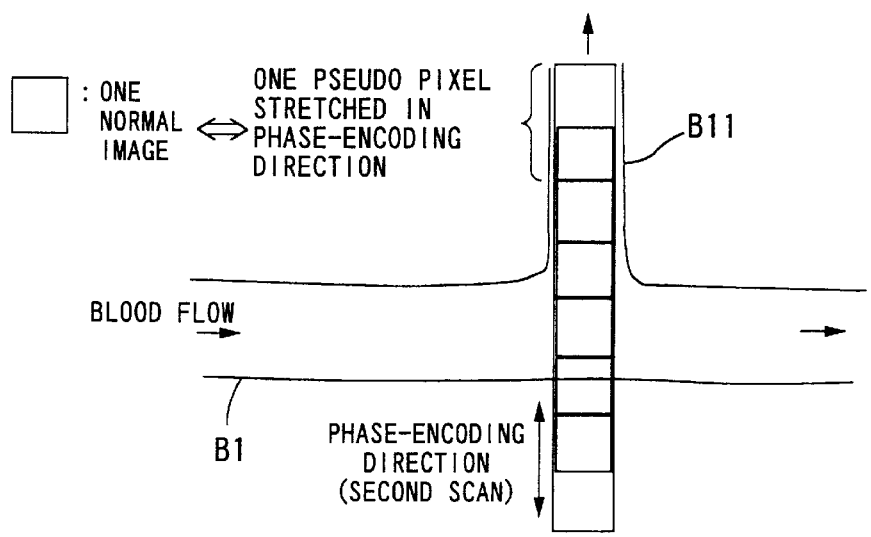
Figure 6C:
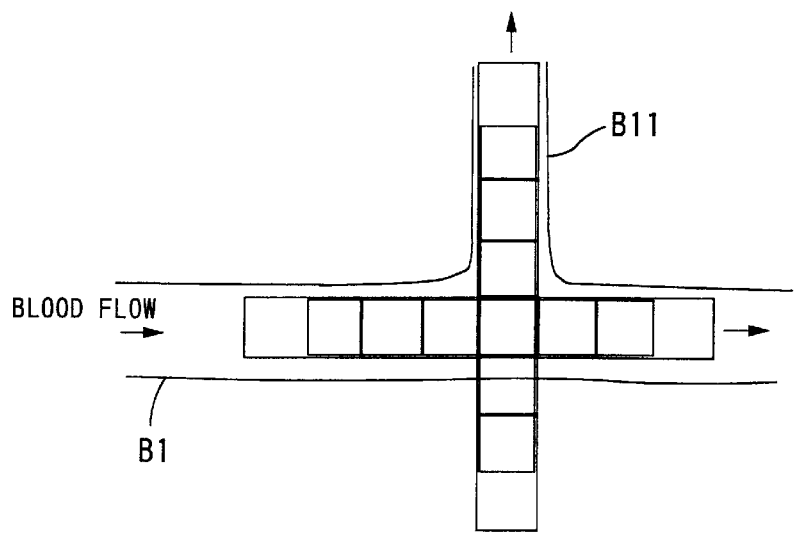

This will be described illustratively in conjunction with FIGS. 6A to 6C. As shown in FIGS. 6A to 6C, assume that a blood vessel B11 is branching out from a vessel B1 in a direction orthogonal to the vessel B1, the phase-encoding direction for the first scan is substantially consistent with the running direction of the vessel B1, and the phase-encoding direction for the second scan is substantially consistent with the running direction of the branching vessel B11. As shown in FIG. 6A, the spread of signal levels along the axis of abscissae indicating a phase-encoding direction for the first scan is equivalent to a situation in which each pseudo pixel is stretched. The vessel B1 running in a direction substantially consistent with the phase-encoding direction is blurred and thus enhanced, while the vessel B11 running in a direction orthogonal to the vessel B1 is simply blurred. However, the phase-encoding direction for the second scan is changed by 90°.

This time, as shown in FIG. 6B, the vessel B1 is simply blurred, while the other vessel B11 is blurred and enhanced.

In the aforesaid embodiment in which the present invention is embodied, the reconstructed images shown in FIGS. 6A and 6B are added up (synthesized) pixel by pixel. Both the blood flows B1 and B11 running in the phase-encoding directions do not disappear but remain intact in a synthetic image as shown in FIG. 6C. Moreover, although the blood flows are blurred in the phase-encoding directions, since the two images are added up pixel by pixel during addition, the advantage of the averaging technique can be exerted. Besides, signal levels induced by a blood flow are raised in order to improve a signal-to-noise ratio. Visualization of two crossing directions is described with reference to FIGS. 6A to 6C. Even if the blood flow B1 is deviated slightly from the phase-encoding direction set for the first scan or the blood flow B11 is deviated slightly from the phase-encoding direction set for the second scan, the above advantage can be exerted. Vessels such as the pulmonary vessels running vertically and laterally can be visualized at a high signal-to-noise radio and a high contrast relative to the parenchyma with almost no loss of information concerning the running directions of the vessels. This can contribute to improvement of diagnostic performance.

In the case of the known averaging technique in which a phase-encoding direction is fixed, a signal-to-noise ratio is expected to be improved. However, when the phase-encoding direction is set to, for example, the direction shown in FIG. 6A, the blood flow B11 may become indiscernible because of the blur in the phase-encoding direction or may disappear. When the phase-encoding direction is set to the direction shown in FIG. 6B, the blood flow B1 confronts with the similar problem. However, the present invention makes it possible to avoid the situation and visualize vessels exhibiting a rather short time $T_2$, such as, the pulmonary vessels and hepatic vessels without a reduction in amount of information concerning the running directions of the vessels.

Figure 7A:
FIGS. 7A to 7C show MRA images of the lungs and the liver produced by conducting an experiment intended to demonstrate the advantages of the present invention.
Figure 7B:
Figure 7C:
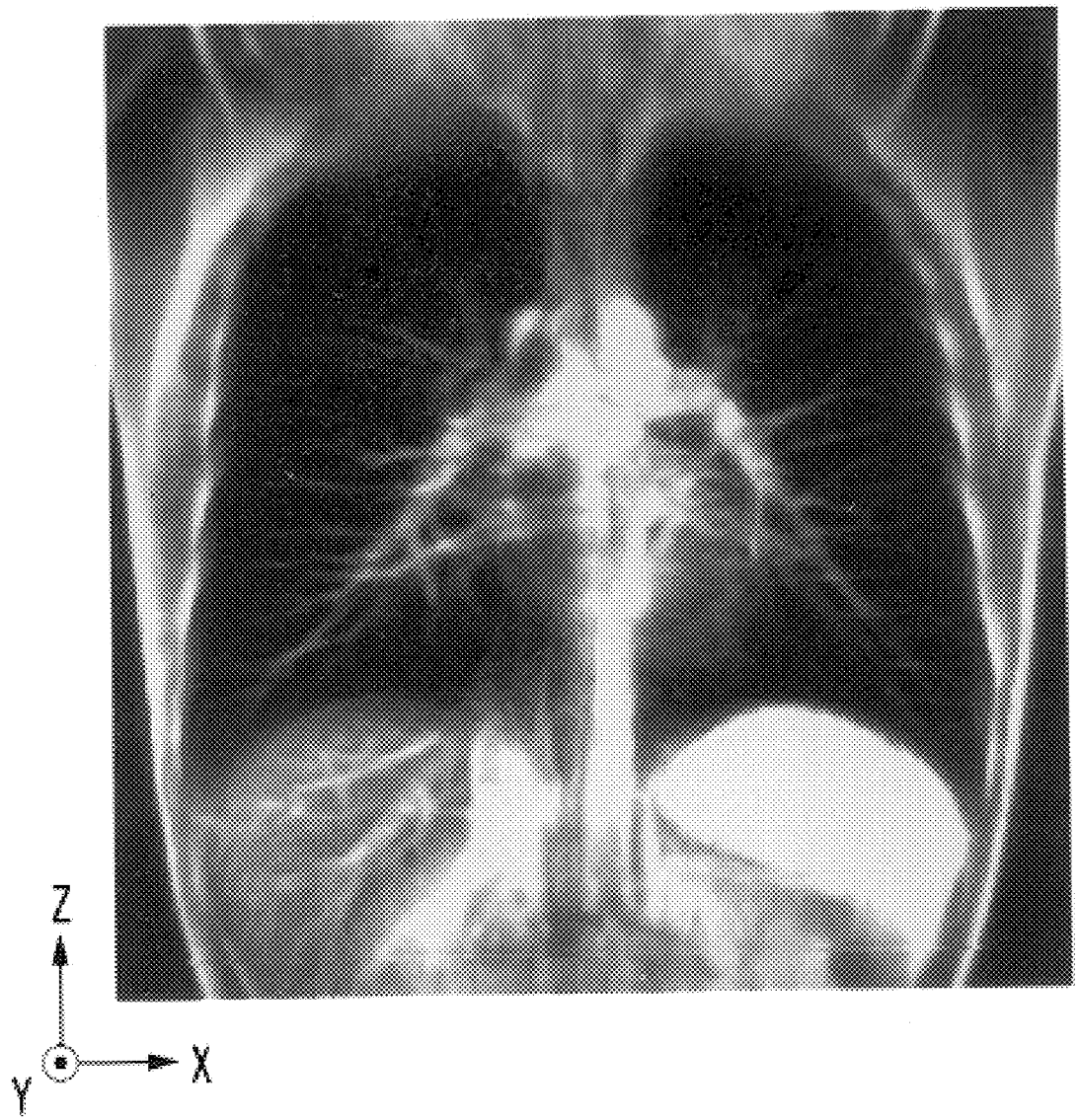

FIGS. 7A to 7C show coronal images produced during an experiment conducted by the present inventor according to the present invention. In FIG. 7A, the phase-encoding direction is set to the Z-axis direction, and the readout direction is set to the X-axis direction. In FIG. 7B, the phase-encoding direction and readout direction are set to the opposite directions respectively. In the drawings, the slice direction is set to the Y-axis direction. This experiment was intended to assess the MRA visualization ability of the MRI system to visualize the lungs and portal vein under the conditions that the two-dimensional FASE imaging was carried out (TEeff= 120 msec, ETS(inter-echo time spacing)=5 msec, the number of shots=1, ST (slice thickness)=30 mm, NS (number of slice)=1, pixel size=256×256, 35×35 cm, actual scan time= 760 msec), a time difference between the start of the first scan to the start of the second scan was 4000 milliseconds, and the phase-encoding direction was changed between two directions as shown in FIGS. 7A and 7B.

As far as the lungs and portal vein in FIGS. 7A or 7B are concerned, it is clearly seen that the blood flows are running in the set phase-encoding direction. By contrast, from the image in FIG. 7C produced by adding up the images shown in FIGS. 7A and 7B, it is clearly seen that the vessels are running vertically and laterally. In short, the image of FIG. 7C provides abundant information of the running directions of the vessels and reflects precisely the actual vessels. Thus, it is recognized that the image of FIG. 7C produced according to the technique of the present invention gains an advantage over the conventional images (images resulting from averaging in FIGS. 7A and 7B). The outstanding effect of the present invention has been identified.

Figure 8:
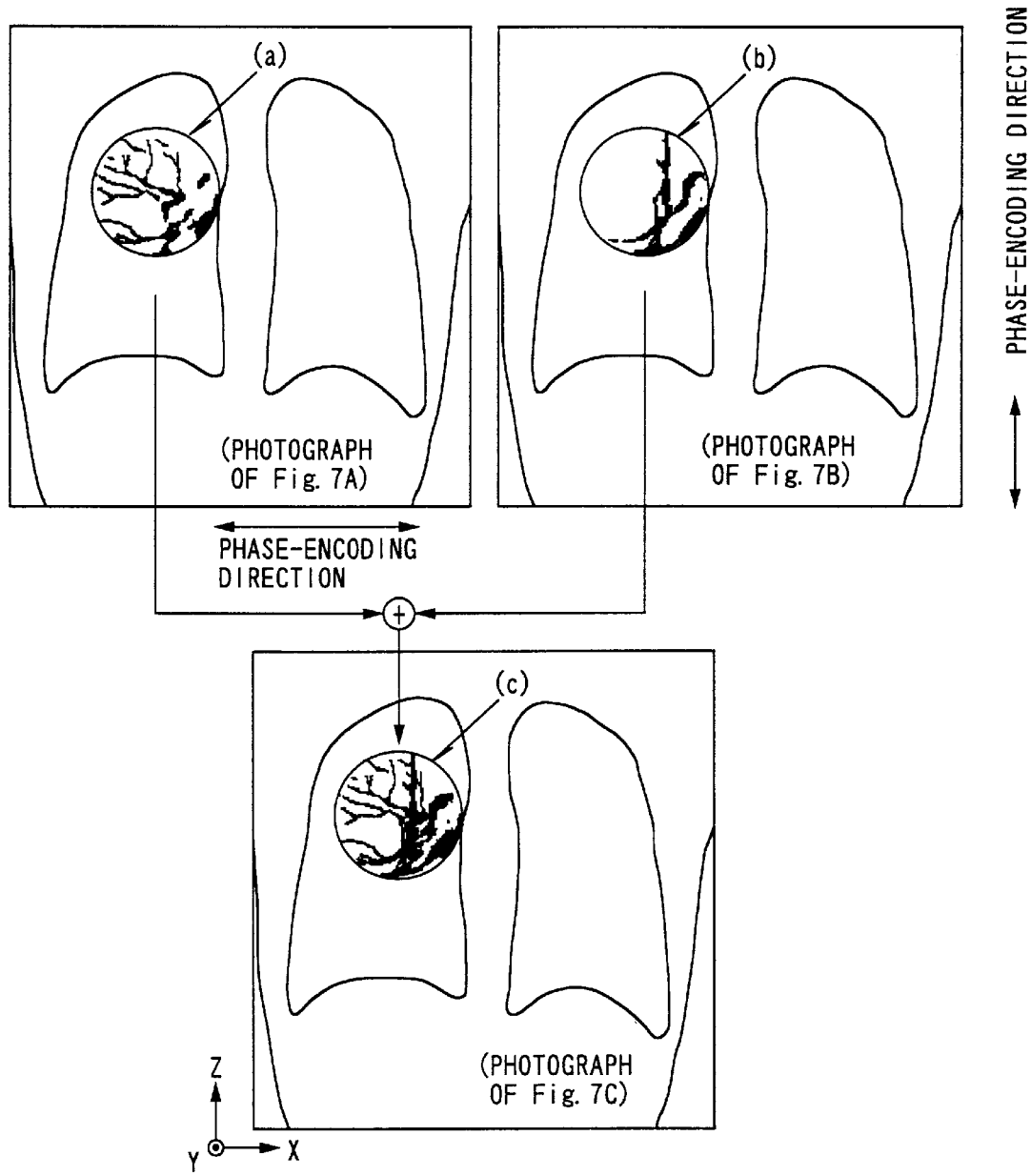
FIG. 8 is a hand-written diagram for pictorially explaining the advantages of the present invention in the same round region arbitrarily pointed in the lungs shown in FIGS. 7A–7C.

For the sake of pictorial explanation of FIGS. 7A to 7C, a circular region, as represented by circles in FIG. 8, is locally placed at the same arbitrarily-selected position on each of FIGS. 7A to 7C and discernible portal veins in each region are hand-traced. A portal vein image in the local circular region (a) in FIG. 7A and a portal vein image in the local circular region (b) in FIG. 7B are added up to form a portal vein image in the local circular region (c) in FIG. 7C. These hand-traced images help to more distinguishably demonstrate differences in the running directions of the portal veins between FIGS. 7A and 7B, thereby again demonstrating the foregoing advantages of the present invention.

In the aforesaid embodiment, all two scans are completed during one period of breath hold. Occurrence of artifacts caused by the periodic motion of the lungs or the like can be suppressed. Besides, occurrence of body-motion artifacts caused by the displacement of a patient's body occurring when the patient is asked to hold breathing a plurality of times can be minimized. Thus, a high-quality image with few artifacts can be produced.

Moreover, since a standby time during which relaxation of spins is awaited is spent between two scans, the second scan can be carried out precisely. A high-quality image can be produced.

Furthermore, although the standby time is set, since the first and second scans each require about 1.5 seconds and the standby time is about 4 seconds, the period of breath hold is about 6 seconds. The duration during which a patient must hold breathing is so short that the mental and physical loads concerning breath hold to be incurred by even a child or a senile person are light. This is advantageous.

Figure 9:
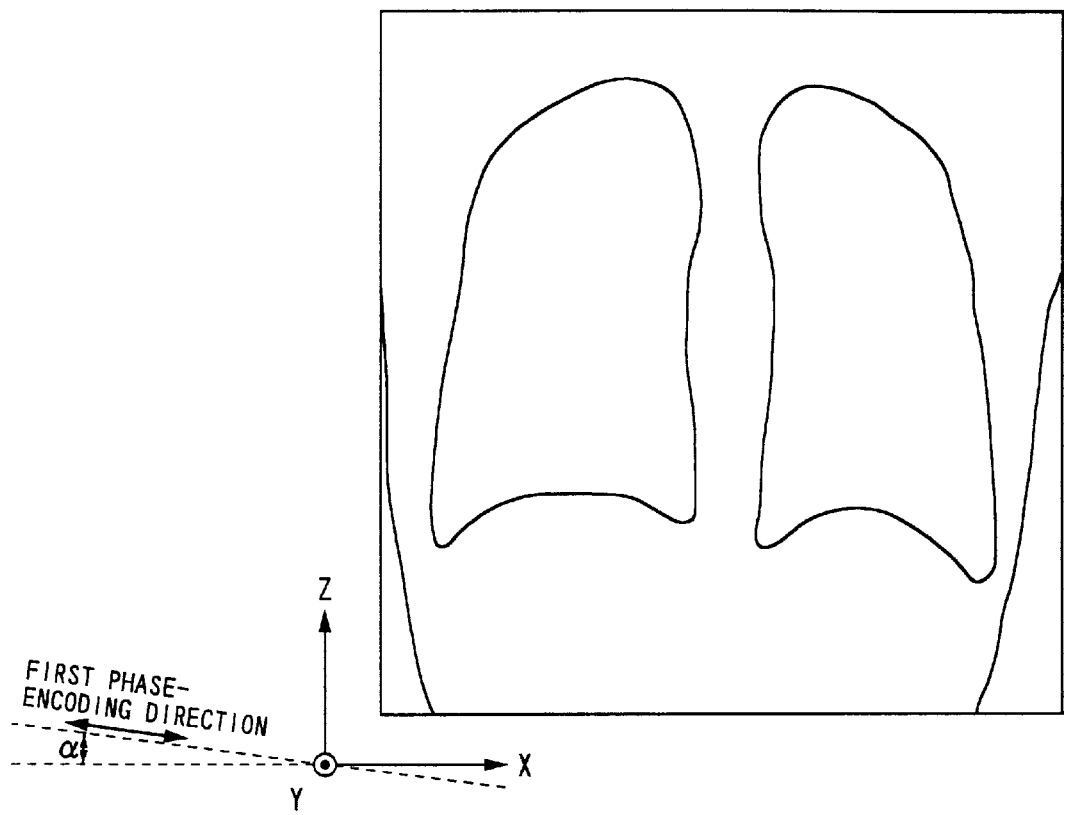
FIG. 9 is an explanatory diagram for explaining the fist phase-encoding direction intentionally set along a selected blood flow direction in the subject in one modification of the first embodiment.

A modification of the first embodiment is shown in FIG. 9. In this modification, the direction of the first phase-encoding gradient among a plurality of times of phase-encoding gradients is intentionally (or positively) set along a certain running direction of veins to be imaged mainly. For example, if portal veins which run obliquely by α degrees are main objects, as shown in FIG. 9, the setting of the direction of the phase-encoding gradient is easily executed by the controller 6 in a manner that intensity ratios among gradients in X-, Y-, Z-axes are adjusted to produce a synthesized gradient for the phase-encoding in the α-degree oblique direction.

In the case of an MRI system according to the modification, desired veins running in the α-degree oblique direction are enhanced by blurring above described. A plurality of times of phase-encoding gradients are applied in angle-changed directions. Therefore, other veins running in the remaining directions other than the α-degree oblique direction are possible to be enhanced due to blurring as well.

The modification makes sure that significant vessels running along a selected desired direction are necessarily enhanced, in addition to more or less enhancement in remaining directions, with simplicity in designing gradient pulse wave forms. Thus, it is not necessary to use a flow compensation technique (for example, refer to R. S. Hinks et al, Magn. Reson. Med. (MRM) 32:698–704(1994)) requiring complicated wave form design of gradient pulses.

(Second Embodiment)

Figure 10:
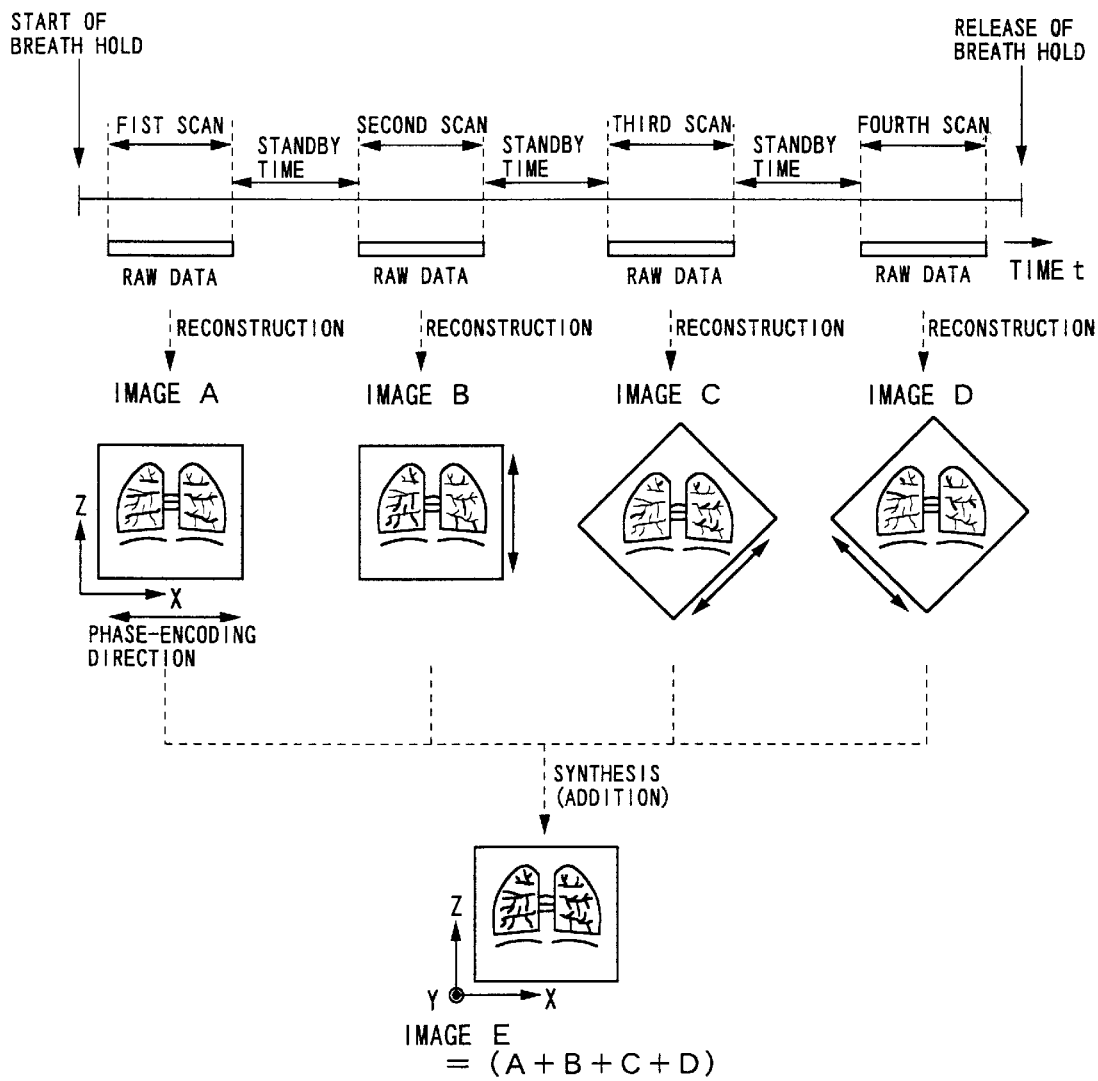
FIG. 10 is a diagram for illustratively explaining the relationship between a scanning sequence and image synthesis in a second embodiment of the present invention.

A second embodiment of the present invention will be described. In the aforesaid first embodiment, two scans are carried out by changing phase-encoding directions. The present invention is not limited to this mode. For example, as shown in FIG. 10, four scans may be carried out successively with a given standby time set between scans while phase-encoding directions are changed for each scan from each other. MR raw data of four frames encoded in the different phase-encoding directions shifted by 45° is thus produced. The raw data of each frame is processed to reconstruct an image, and four reconstructed images are synthesized (by performing addition or maximum intensity projection). This procedure can also provide an MR image containing abundant information of running vessels owing to finer angle control of the phase-encoding direction.

Furthermore, the procedure shown in FIG. 10 may be evolved further. That is to say, while phase-encoding directions are changed for each scan from each other, eight scans are carried out successively with a given standby time between scans. MR raw data of eight frames encoded in the different phase-encoding directions shifted by 22.5° is thus produced, and synthesis is carried out in the similar manner. Namely, the number of images to be added up (synthesized) according to the technique of the present invention (that is, the frequency of changing phase-encoding directions), n, should be equal to or larger than 2.

(Third Embodiment)

A third embodiment will now be described with reference to FIGS. 11 to 13. This embodiment provides a scanning manner employing a combination of both applying the phase-encoding gradient in only one direction (i.e. without image synthesis) and an ECG-gated technique.

Figure 11:
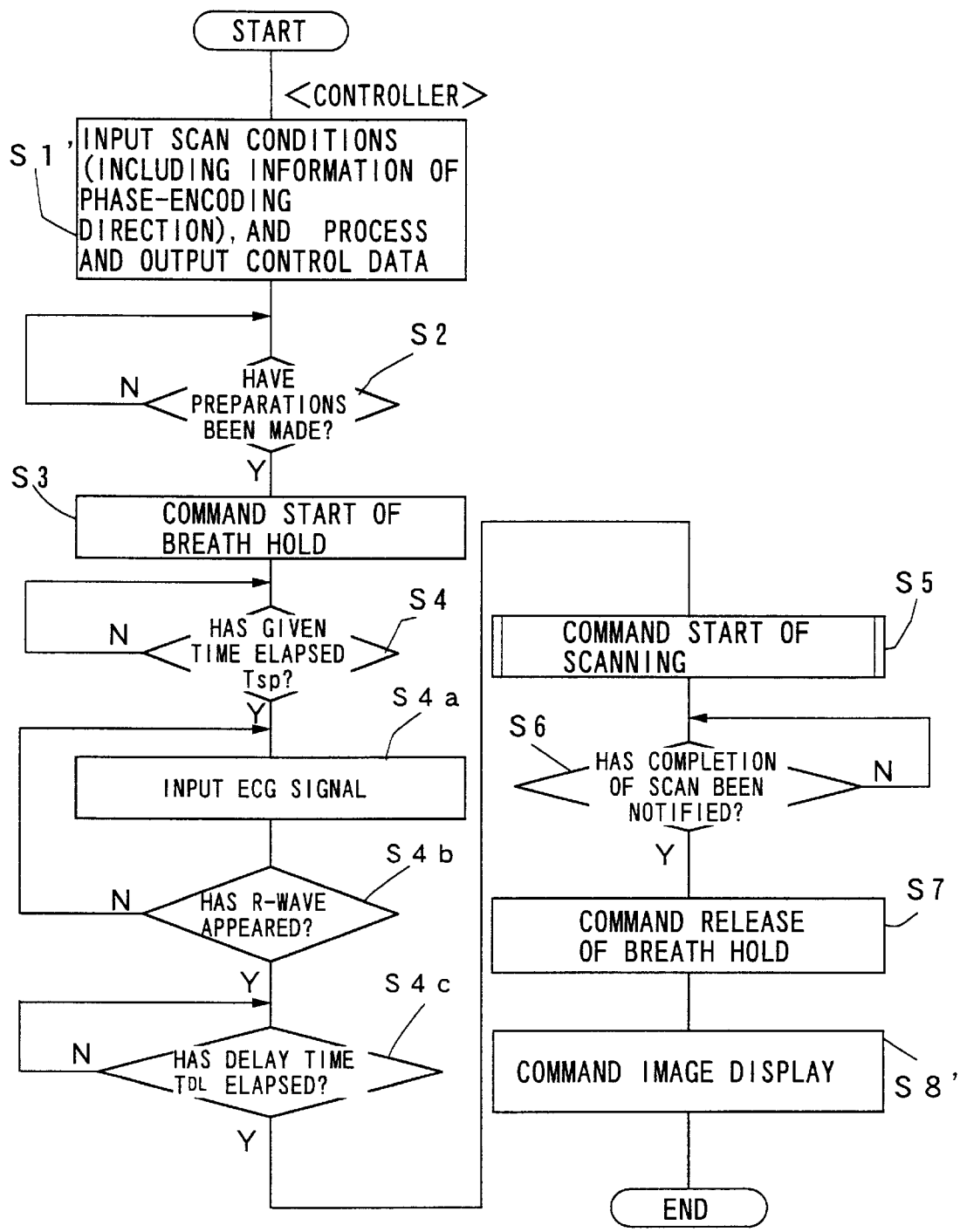
FIG. 11 is a flowchart outlining an example of an imaging procedure to be executed by a controller in a third embodiment.
Figure 12:
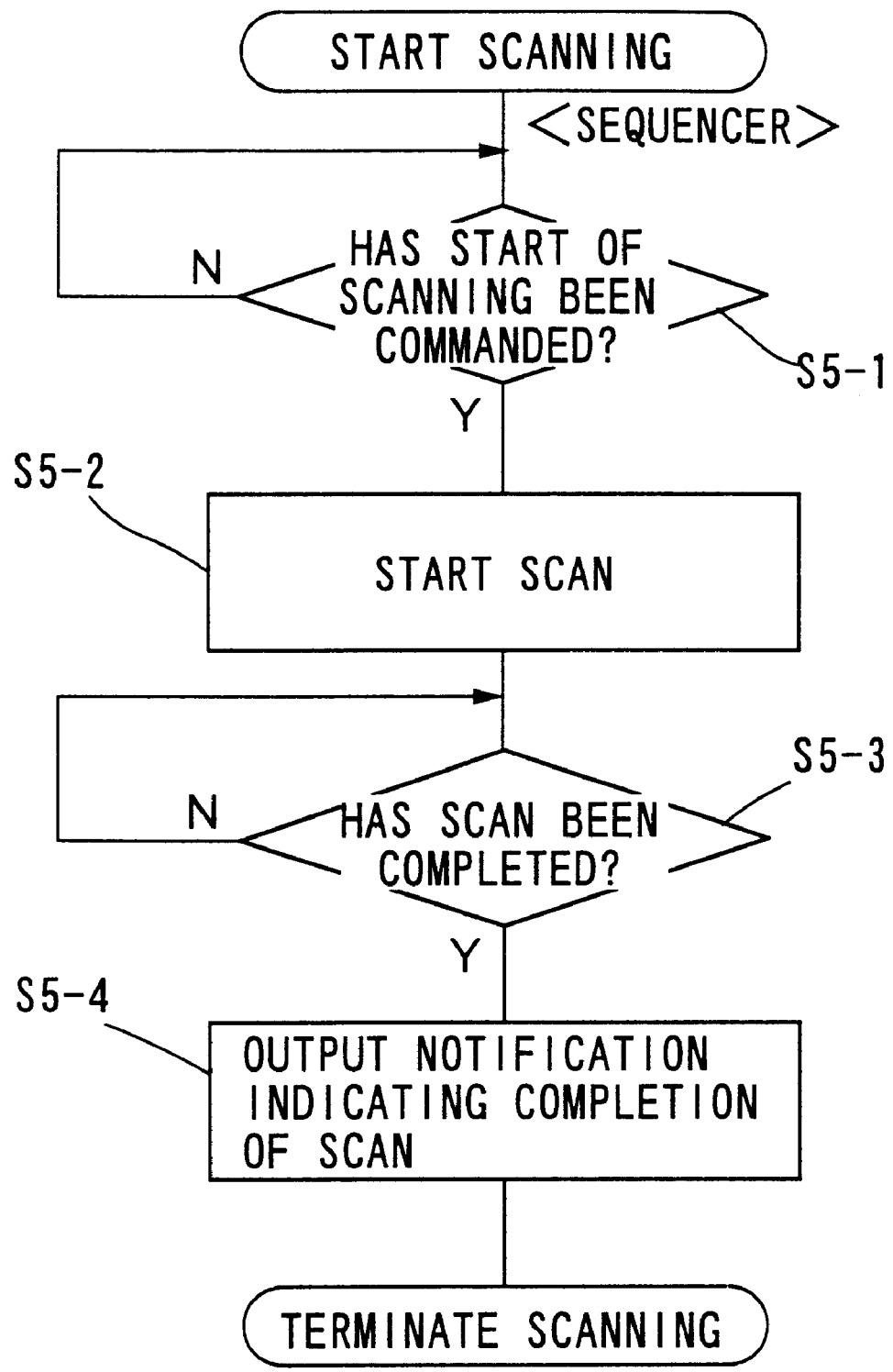
FIG. 12 is a flowchart outlining an example of scan control processing to be executed by a sequencer in the third embodiment.

The controller 6 and sequencer 5 processing shown in FIGS. 11 and 12, respectively. At step S1' in FIG. 11, the controller 6 inputs scan conditions (for example, an image size, information of the phase-encoding direction of one time, and a pulse sequence dependent on a region to be scanned), processes control information according to the input information, and outputs the control information to the sequencer 5 and arithmetic operation unit 10.

After steps S2 and S3 which are the same processing as those in FIGS. 2, a given time-adjusting time Tsp is waited at step S4. After this, processing of steps S4a-S4b follows consecutively, in which an ECG signal supplied by the ECG unit 16 is inputted (step S4a), and whether or not an R-wave peak in the ECG signal has been appeared is determined (step S4b). That is, when the first R-wave occurred, the elapsed time after the command of start of breath hold becomes Tsp' (=Tsp+β, where β is an arbitrary time interval; refer to FIG. 13).

After the appearance of the first R-wave, a delay time $T_{DL}$ is waited (step S4c). The delay time $T_{DL}$ (for example, $T_{DL}$ =500 msec for a cardiac cycle of approximately 700 to 1000 msec) is pre-set to an appropriate time permitting to avoid an unstable blood flow state in and immediately after occurrence of R-waves caused by the cardiac contraction. Specifically, setting an appropriate delay time $T_{DL}$ permits echoes acquired during a relatively stable cardiac period in the diastole etc. to be mapped in the center range or thereabout (i.e., a range of lower frequencies) in the phase-encoding direction of the k-space. Thus, even when one scan lasts over the next one or more appearances of the R-wave, echoes acquired in the systole can be mapped in the end ranges or thereabout (i.e., a range of higher frequencies) in the phase-encoding direction of the k-space. This provides higher contrast and higher quality with reconstructed final images.

When the given delay time $T_{DL}$ has elapsed, processing of steps S5 and S6, which are similar to those in FIG. 2, is executed. In response to the scan command, the sequencer 5 executes one time acquisition of a set of MR raw data (FIG. 12; steps S5-1 to S5-4).

When the scanning has completed, the controller 6 commands the stop of breath hold and display (reconstruction) of a scanned image (steps S7 and S8'). At step S8', a command of the image synthesis processing described before is avoided.

Figure 13:
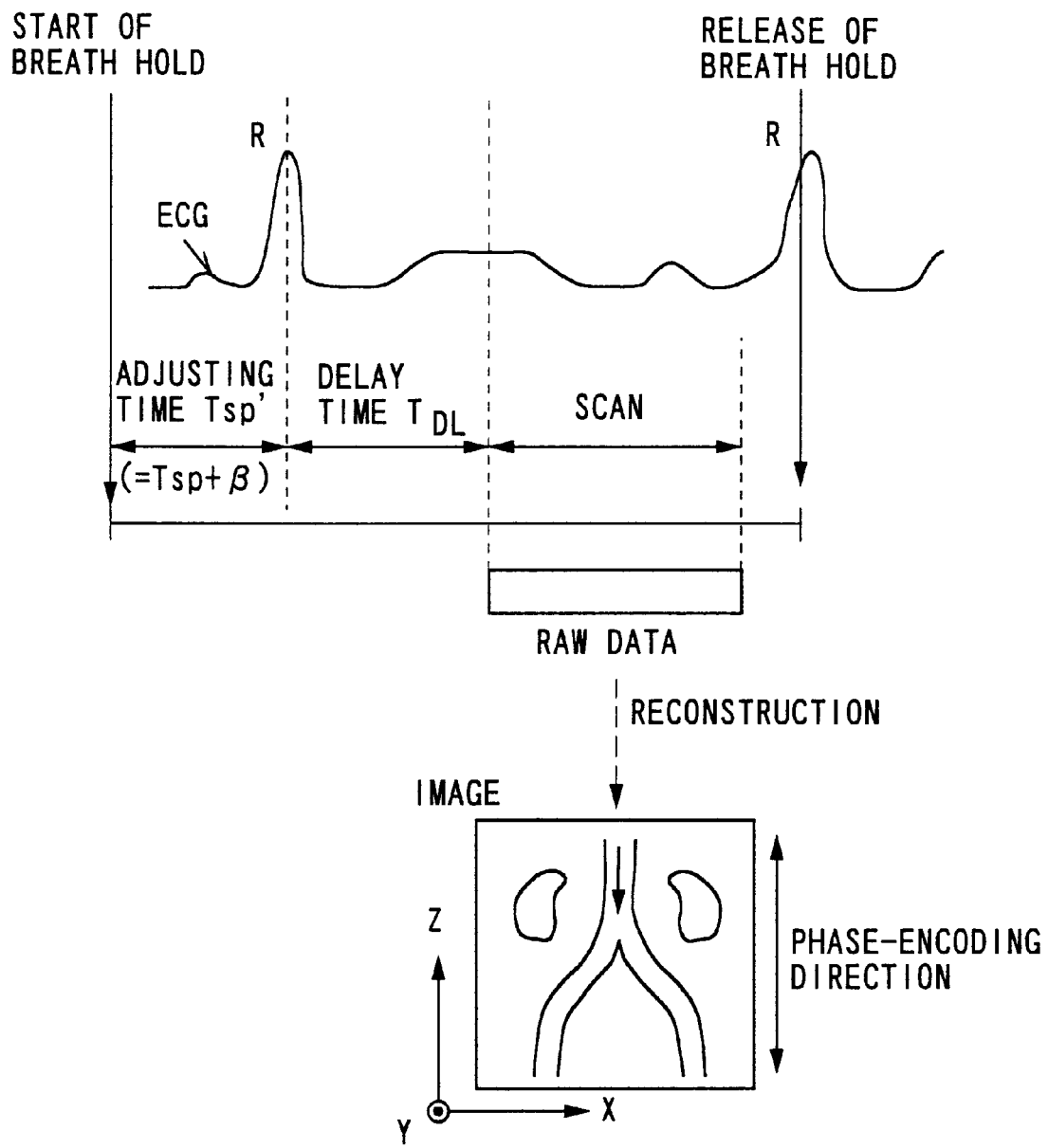
FIG. 13 is a diagram for illustratively explaining the relationship between a scanning sequence and image production in the third embodiment.

FIG. 13 shows one example of a timing chart according to this embodiment wherein MR raw data acquisition is carried out in only one phase-encoding direction. Therefore, this embodiment is preferable when a running direction of vessels to be imaged in a subject's region is known or can be supposed beforehand. For example, blood vessels in the hypogastrium can properly be applied to this scanning. When scanning is carried out with this technique according to the third embodiment, the phase-encoding direction is controlled to a known or supposed running direction of vessels to be imaged. This also makes it possible to enhance desired vessels in a reconstructed image according to the foregoing same principle even when the image synthesis is omitted. In consequence, a flow compensation technique is unnecessary.

Further the ECG-gated technique provides an advantage that MR images having a higher and more steady contrast MR image are produced. Appropriately adjusting the delay time $T_{DL}$ between the R-wave and the scan can bring the whole scan interval into desired temporal positions which can avoid disturbance in blood flows due to the contraction of the cardiac. Echo signals acquired in the beginning part of the scan are mapped in the center region in the phase-encoding direction of the k-space for reconstruction. The signal intensities mapped in the center portion are decisive for contrast of reconstructed images. In this embodiment, echo signals in the beginning part can be acquired in an adequate timing zone in variations of blood flow, and mapped in the center region of the k-space. This provides steady and stable contrast of MR images.

There are additional advantages resulting from the breath hold and one time of scanning (i.e., shorter scan time in total).

(Fourth Embodiment)

A fourth embodiment will now be explained in conjunction with FIGS. 14 to 16. This embodiment employs an ECG-gated technique in the MRI system described in the first embodiment.

Figure 14:
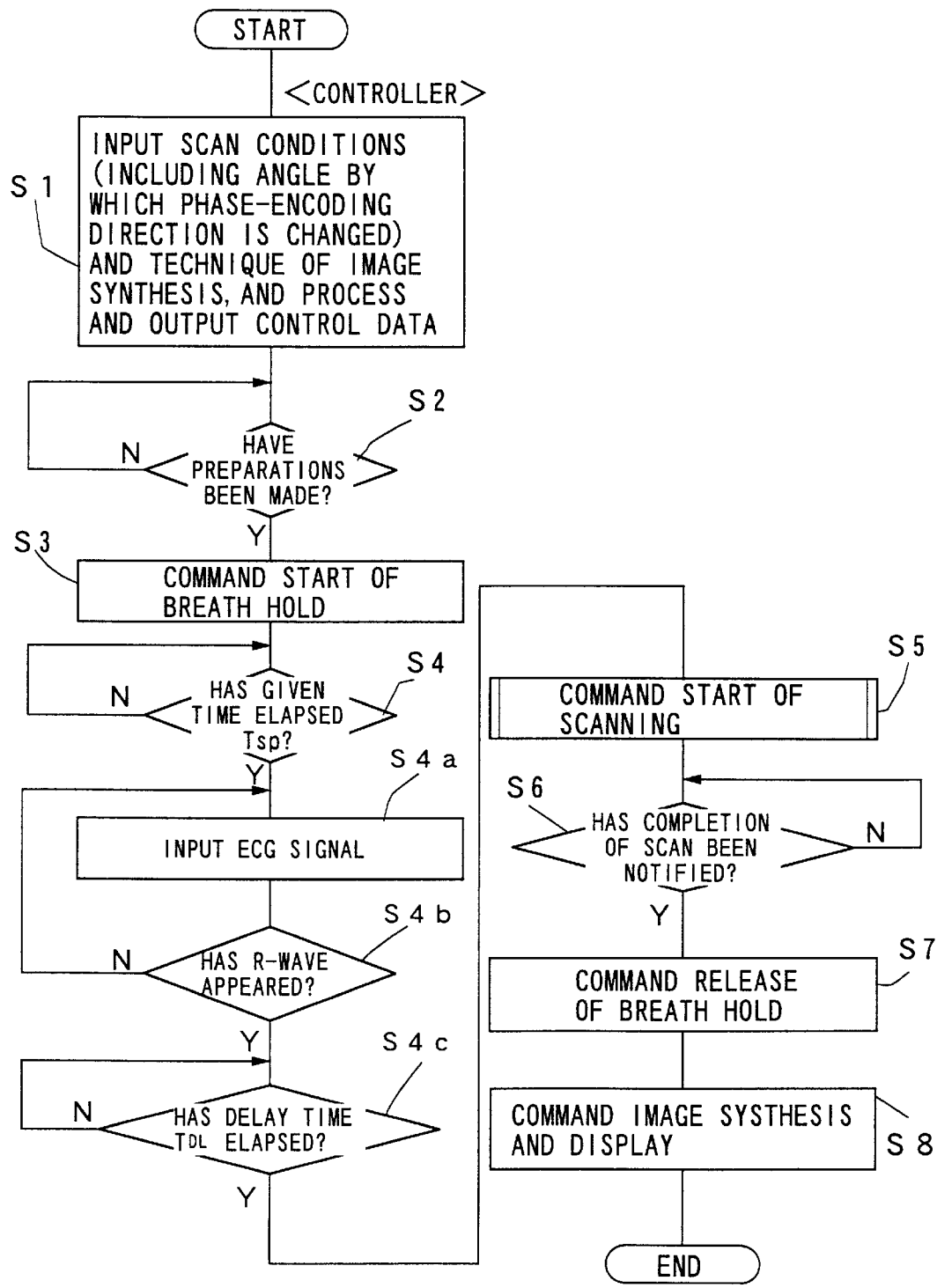
FIG. 14 is a flowchart outlining an example of an imaging procedure to be executed by a controller in a fourth embodiment.
Figure 15:
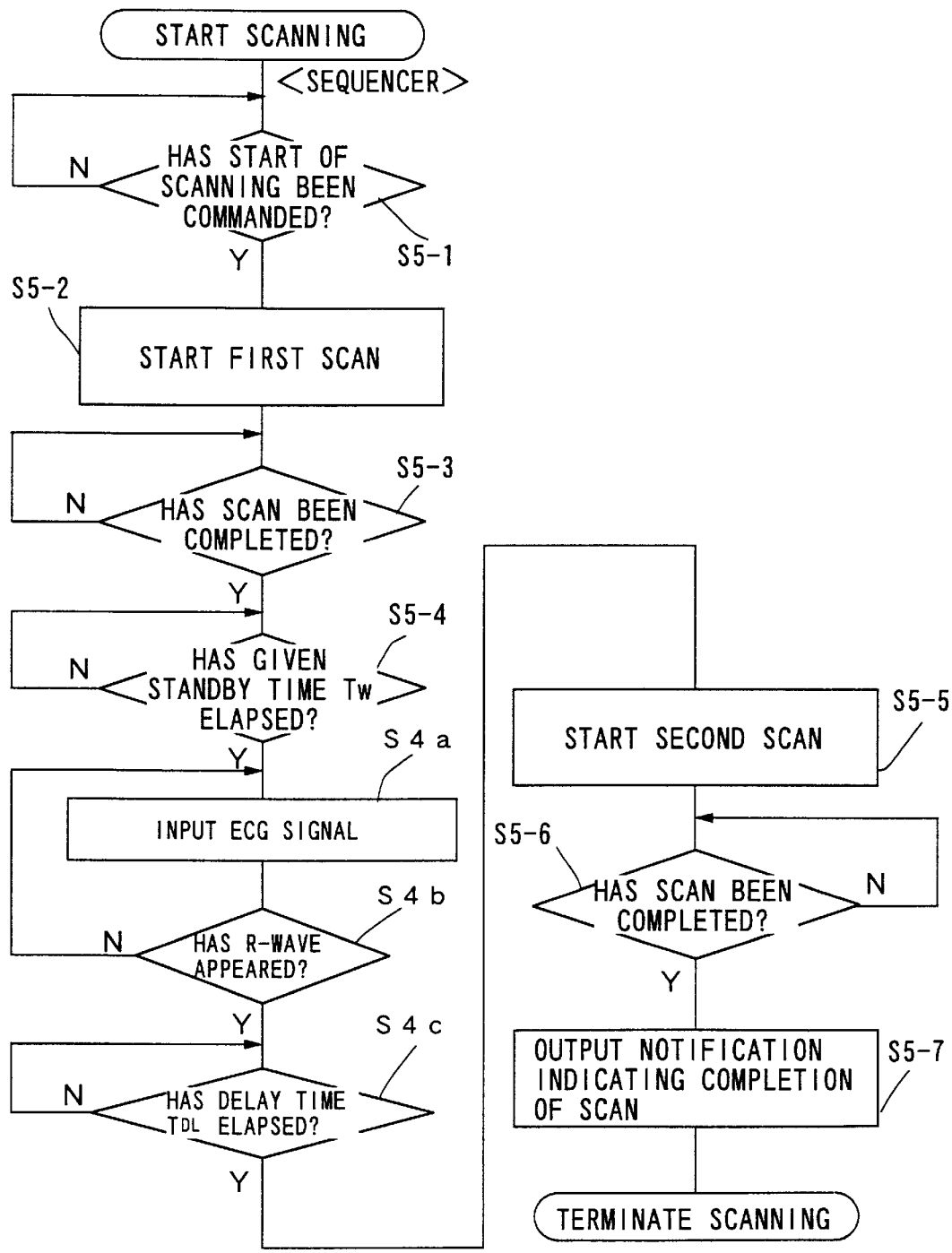
FIG. 15 is a flowchart outlining an example of scan control processing to be executed by a sequencer in the fourth embodiment.

The controller 6 and sequence 5 are designed to execute processing shown in FIGS. 14 and 15, respectively, wherein steps S4a to S4c and steps S5-4a to S5-4c are newly added.

Figure 16:
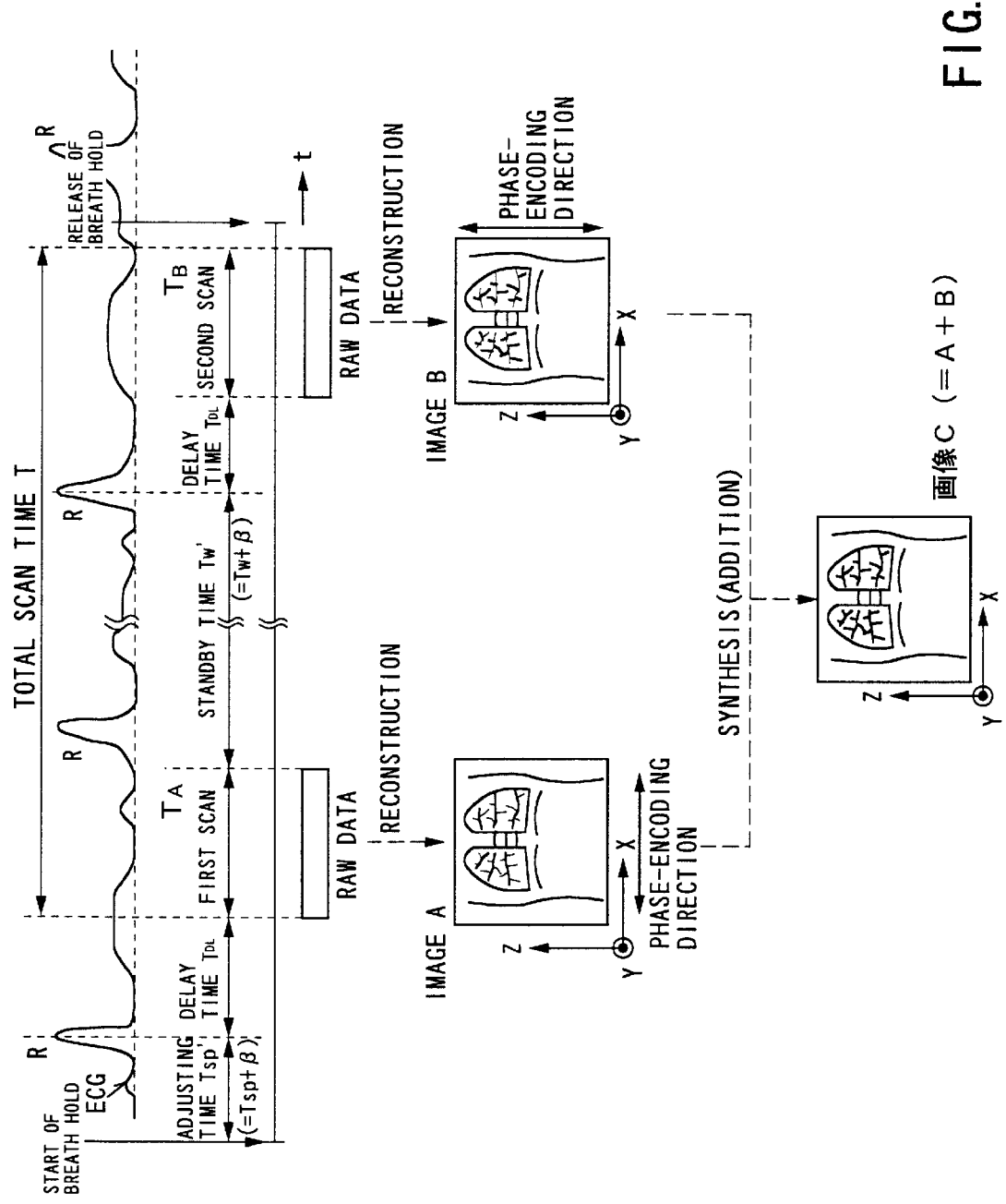
FIG. 16 is a diagram for illustratively explaining the relationship between a scanning sequence and image synthesis in the fourth embodiment.

Processing at steps S4 and S4a, S4b in FIG. 14 permits to set an adjusting time $T_{sp}'$ (=a given time $T_{sp}$+an arbitrary time β) between the start of breath hold and the first R-wave appeared for the first time after completion of the given time interval $T_{sp}$ (refer to FIG. 16). Processing at step S4c gives a specified delay time for the ECG gate before the first scan, as shown in FIG. 16.

Furthermore, processing at steps S5-4a and S5-4b in FIG. 15 gives rise to a standby time Tw' (=a given standby time Tw+an arbitrary time β) between the end of the first scan and the first R-wave appeared for the first time after the elapse of the given standby time Tw (refer to FIG. 16). Also processing at step S5-4c provides a specified delay time for the ECG gate before the second scan, as shown in FIG. 16.

The remaining processing is the same as that in the first embodiment.

Therefore, employing the ECG-gated technique additionally provides a more steady contrast of images as described above.

(Fifth Embodiment)

A fifth embodiment will now be explained in conjunction with FIGS. 17–18A and 18B. This embodiment is concerned with three-dimensional(3D) imaging into which the present invention is applied.

In the case of three-dimensional scanning, for example, a plurality of scans are carried out with the slice direction unchanged while the phase-encoding direction and readout direction are changed for each scan. Thus, the technique of the present invention can be implemented effectively.

Figure 17:
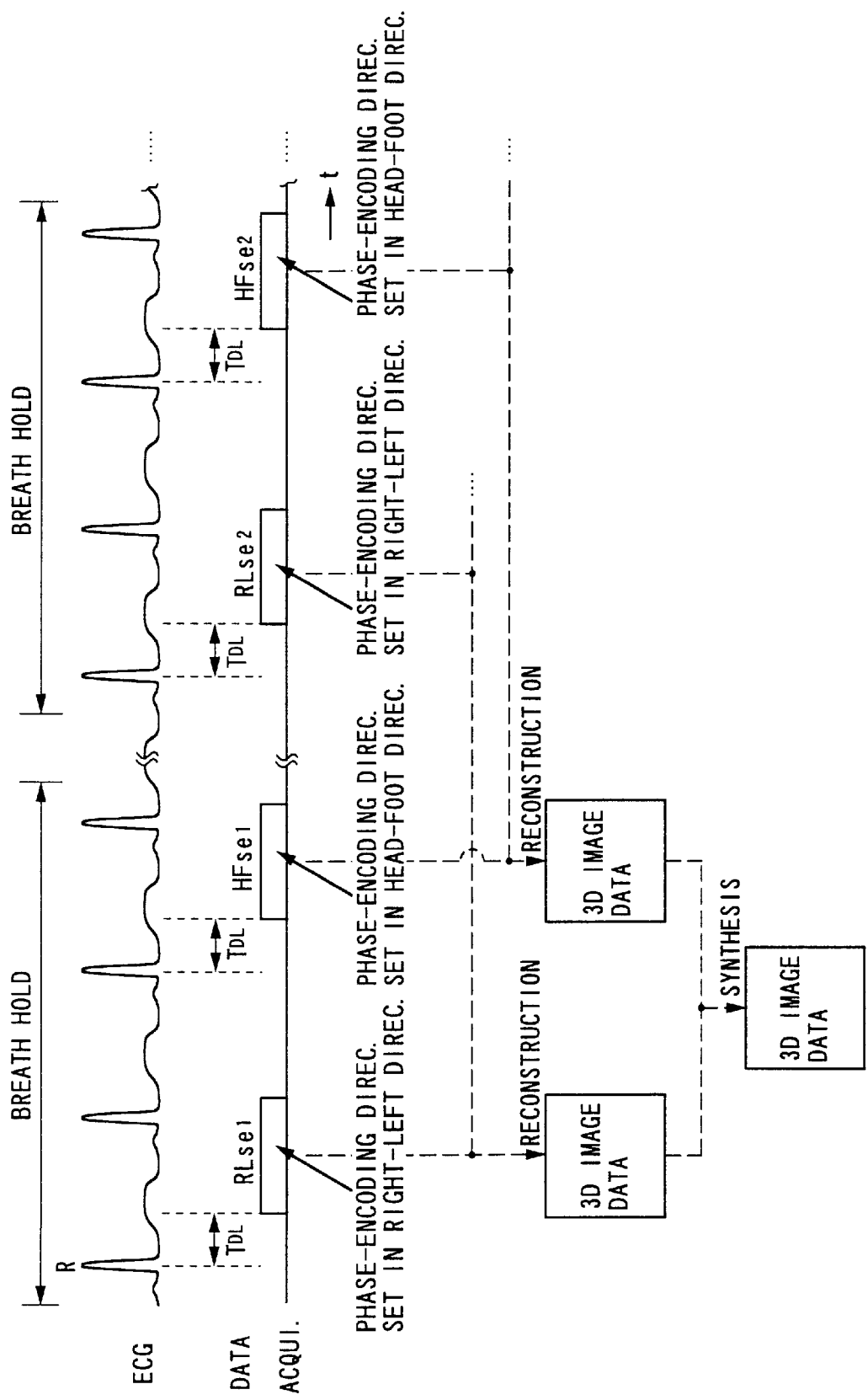
FIG. 17 is a diagram for illustratively explaining the relationship between a scanning sequence and image synthesis in a fifth embodiment.
Figures 18A, 18B:
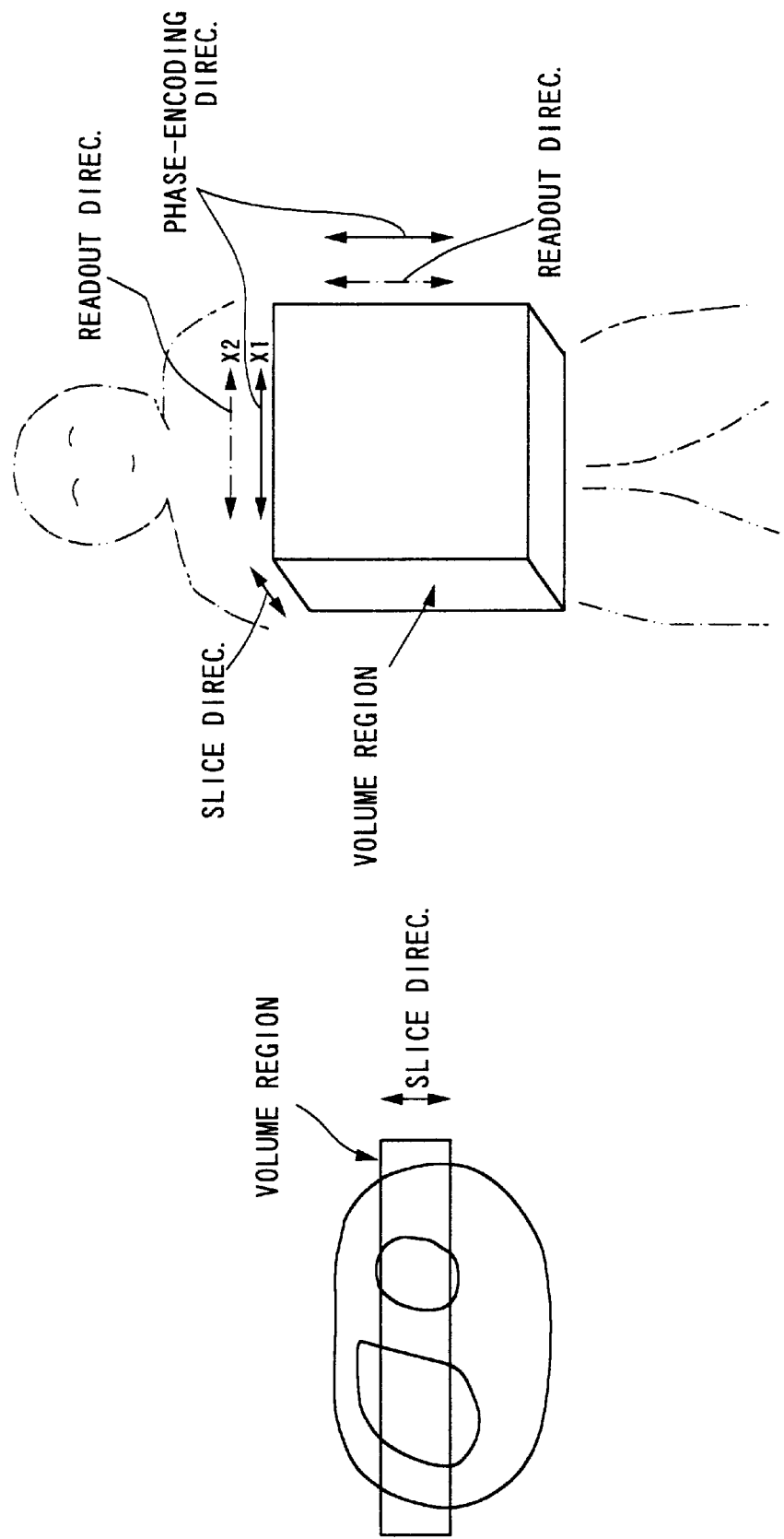
FIGS. 18A and 18B explain pictorially a three-dimensional volume to be scanned in a patient.

Specifically, FIG. 17 shows one example of a data acquisition sequence instructed by the controller 6 and sequencer 5, which uses ECG-gated and breath hold techniques described above, as well as the phase-encoding direction change technique. For example, for hypogastrium to be three-dimensionally imaged, as shown in FIGS. 18A and 18B, data acquisition of a volume is carried out 2n-times (n: integer lager than 1) in the order of each scan of RLse1, HFse1, RLse2, HFse2, . . . , RLsen, and HFsen.

The can "RL" and "HF" represent ECG-gated single scan for one of the slice-encoding gradient amounts providing three-dimensional raw data of the volume to be imaged, but those scans are different in the phase-encoding direction. In the case of RL (right-left) scanning, the phase-encoding direction is set in the right-left direction to a patient, as shown by solid arrow X1 in FIG. 18B, while in the case of HF(head-feet) scanning, the phase-encoding direction in the head-feet direction to a patient, as shown by a dotted arrow X2 in FIG. 18B, which differs by 90 degrees from the solid arrow X1. The subscripts "se1, . . . , sen" of RL and HF represent slice-encoding whose slice-encoding gradient amounts are changed for each scan. In the exemplified sequence, the first and second ECG-gated scans are carried out for the same slice-encoding gradient amount "se1 (se2, . . . , sen)". And those two scans are repeated with changed gradient amounts of the slice-encoding. As for breath hold in this 3D imaging, as the whole scan period become a relatively longer, it is divided into several times.

One set of 3D image data are reconstructed from a group of raw data acquired from the scanning whose phase-encoding direction has been set in the right-left direction, while the other set of 3D image data are reconstructed form those acquired from the scanning whose phase-encoding direction has been set in the head-feet direction. Both the 3D image data are synthesized pixel by pixel, as described by addition and the like.

Thus, one 3D image is formed using a combination of changed phase-encoding directions, RCG gating, and breath hold techniques, providing the same or similar advantages as or to those in described above. This 3D imaging can be carried out in various modified forms, such as more than two-times changes in the direction of the phase-encoding direction. Of course, any scan pulse sequence described above can be used herein.

(Sixth Embodiment)

A sixth embodiment will now be explained in conjunction with FIGS. 19 and 20. This embodiment is concerned with multi-slice imaging into which the present invention is also applied.

Figure 19:
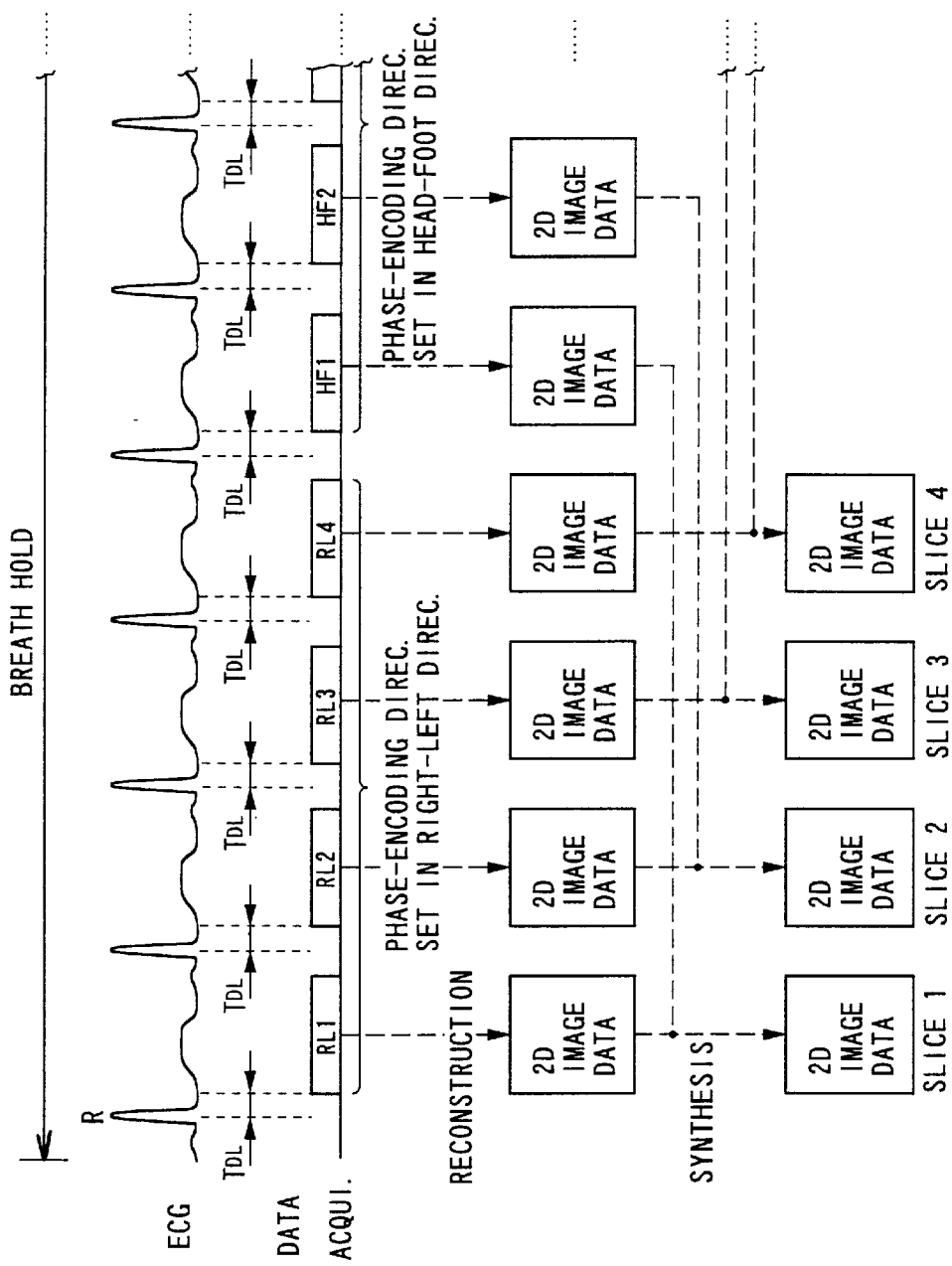
FIG. 19 is a diagram for illustratively explaining the relationship between a scanning sequence and image synthesis in a sixth embodiment.
Figure 20:
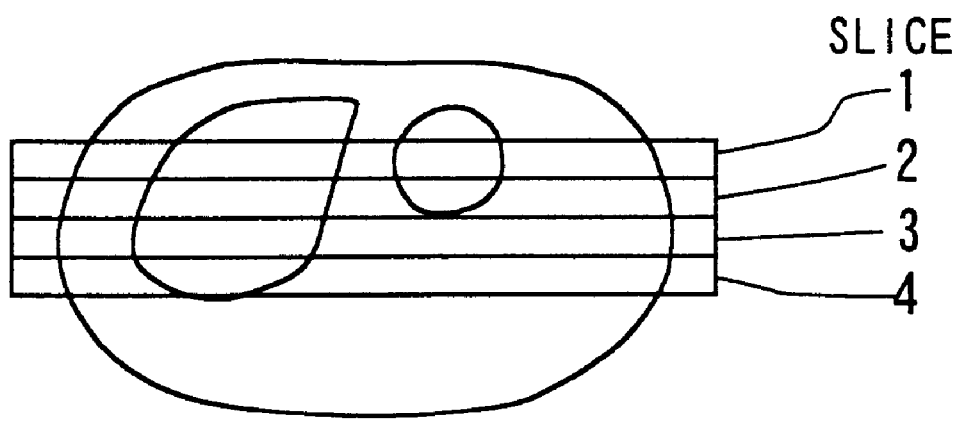
FIG. 20 explains pictorially a multi-sliced region to be scanned in a patient.

FIG. 19 exemplifies a data acquisition sequence instructed by the controller 6 and sequence 5, which uses controlled setting of the phase-encoding directions, ECG-gating, and one time of breath hold. For example, for hypogastrium to be multi-slice imaged (e.g., four slices), as shown in FIG. 20, raw data acquisition is done in the order of RL1, RL2, RL3, RL4, HF1, HF2, HF3, and HF4. The scans of RL and HF are for the phase-encoding directions set in the right-left direction and head-feet direction of a patient, respectively, and produce one frame of raw data being reconstructed. For each slice, two frames of 2D reconstructed image data, the phase-encoding directions of which differ by 90 degrees mutually, are synthesized pixel by pixel, thus providing higher detectability of blood flows, as described before. Of course, the other advantages concerning ECG gating and breath hold are provided in this embodiment, Additionally any number of slices can be selected in this multi-slice imaging.

By the way, the order of the scans is not limited to the exemplified one in the above embodiment. It may be changed into any order according to the design of multi-slice imaging, such as an interleaved one like RL1, HF1, RL2, HF2, etc. In this case of the alternatively-changed interleaved order, both the scans of RL and HF for each slice can be performed in the nearest cardiac time phase, providing being less pixel-positional sifts, caused by the body motion and the like, between the two frames of image data synthesized.

Moreover, in the above fifth and sixth embodiments, the synthesis has been made with two sets (or frames) of reconstructed image data resultant from two phase-encoding directions mutually changed by 90 degrees. Alternatively, the synthesis can be made based on three or more sets (or frames) of reconstructed image data when the phase-encoding direction being changed in angle into three or more ways.

Of course, like the third embodiment, the fifth and sixth embodiments can be carried out without changing the phase-encoding direction for each finally produced image. In this case, imaging can be done without the synthesis of image data, with only ECG gating and/or breath hold techniques employed. Even if such simplified imaging is done, it is preferred to set the direction of phase-encoding in a desired direction, like the foregoing modification in FIG. 9.

Furthermore, the foregoing various embodiments are concerned with MRA. An object of imaging is not limited to vessels but may be any entity such as a tissue running like a fiber. As long as an entity is composed of spins whose time $T_2$ is rather short, the scanning and image processing in accordance with the present invention can preferably be implemented in imaging the entity.

Further, in the fifth and sixth embodiments, the delay time $T_{DL}$ (for example, 500 msec) from the R-waves of the ECG signal can be determined like being described in the third embodiment.

Although the description above contains many specificities, these should not be construed as limiting the scope of the invention but as merely providing illustrations of some of the presently preferred embodiments of this invention. Thus the scope of this invention should be determined by the appended claims and their equivalents.

What is claimed is:

1. An MRI system for providing an image of a subject through scanning based on a pulse sequence, including pulsed gradients applied to the subject in a phase-encoding read-out, and slice directions set to the subject, comprising:

means for acquiring a plurality of sets of MR raw data by performing a plurality of scans on a region of interest to be imaged of the subject with the pulse sequence, the acquiring means including means for controlling the phase-encoding direction for at least one scan selected from the plurality of scans so as to be spatially changed with resepect to the other plurality of scans; and means for producing data of the image from the plurality of sets of the MR raw data.

2. The MRI system of claim 1, wherein the producing means comprises means for reconstructing each of the plurality of sets of MR raw data into a set of image data in a real space, and means for synthesizing the plurality of sets of reconstructed image data into the data of the image.

3. The MRI system of claim 2, wherein the acquiring means includes means for setting the region of interest to be imaged to a single two-dimensional slice by controlling the pulsed gradient applied in the slice direction.

4. The MRI system of claim 2, wherein the acquiring means includes means for setting the region of interest to be imaged to a multi-sliced region including a plurality of two-dimensional slices by controlling the pulsed gradient applied in the slice direction.

5. The MRI system of claim 2, wherein the acquiring means includes means for setting the region of interest to be imaged to a three-dimensional volume by controlling the pulsed gradient applied in the slice direction.

6. The MRI system of claim 2, wherein the synthesizing means performs at least one of addition processing and maximum intensity projection processing to the plurality of sets of reconstructed image data to produce the data of the image.

7. The MRI system of claim 1, further comprising means for notifying a patient employed as the subject of a duration of single-time breath hold, wherein the acquiring means is constructed to perform the plurality of scans within the duration of single-time breath hold.

8. The MRI system of claim 1, wherein the acquiring means includes means for standing by during an interval set between temporal neighboring two scans among the plurality of scans, the interval being set to return nuclear spins in the region to be imaged to a steady state thereof.

9. The MRI system of claim 1, wherein the plurality of scans comprise two scans carried out in sequence, and the phase-encoding direction being changed by substantially 90° for each scan.

10. The MRI system of claim 1, wherein the plurality of scans comprises n-times of scans, n being an integer larger than 2, carried out in sequence, and the phase-encoding direction being changed by substantially 180° /n one from another for each scan.

11. The MRI system of claim 1, further comprising means for acquiring an electrocardiograph signal of a patient employed as the subject, wherein the acquiring means includes means for determining a start time of the scan based on the electrocardiograph signal and means for starting the scan at the start time.

12. The MRI system of claim 11, wherein the controlling means includes an element for setting the phase-encoding direction for the first scan among the plurality of scans in a pre-specified running direction of an entity of interest residing within the region to be imaged of the patient.

13. The MRI system of claim 1, wherein the controlling means includes an element for setting the phase-encoding direction for the first scan among the plurality of scans in a running direction of an entity of interest residing within the region to be imaged of the subject.

14. The MRI system of claim 1, wherein the controlling means changes the phase-encoding direction scan by scan into each of predetermined different directions.

15. The MRI system of claim 14, wherein the acquiring means includes means for setting the region of interest to be imaged to a single two-dimensional slice by controlling the pulsed gradient applied in the slice direction.

16. The MRI system of claim 14, wherein the acquiring means includes means for setting the region of interest to be imaged to a three-dimensional volume by controlling the pulsed gradient applied in the slice direction.

17. The MRI system of claim 14, further comprising means for detecting an ECG signal of the subject, the ECG signal including a periodically yielding reference wave, wherein the acquiring means includes means for determining a start time of each scan synchronously with a time delayed by a delay time from the reference wave.

18. The MRI system of claim 17, wherein the delay time is controllable.

19. The MRI system of claim 17, further comprising means for informing a patient employed as the subject of a duration of breath hold, wherein the acquiring means includes means for performing all scans within the informed duration of breath hold.

20. The MRI system of claim 1, wherein the controlling means spatially changes the phase-encoding direction for a certain plurality of scans.

21. The MRI system of claim 20, wherein the acquiring means includes means for setting the region of interest to be imaged to a multi-sliced region comprising a plurality of two-dimensional slices by controlling the pulsed gradient applied in the slice direction.

22. The MRI system of claim 20, further comprising means for detecting an ECG signal of the subject, the ECG signal including a periodically yielding reference wave, wherein the acquiring means includes means for determining a start time of each scan synchronously with a time delayed by a delay time from the reference wave.

23. The MRI system of claim 22, wherein the delay time is controllable.

24. The MRI system of claim 22, further comprising means for informing a patient employed as the subject of a duration of breath hold, wherein the acquiring means includes means for performing all scans within the informed duration of breath hold.

25. An MRI system for providing an image of a subject through scanning based on a pulse sequence including pulsed gradients applied to the subject in a phase-encoding direction set to the subject, comprising:

means for acquiring MR raw data by performing a scan on the subject with the pulse sequence in which the phase-encoding direction is pre-specified along a running direction of an entity of interest residing within a region of interest to be imaged of the subject; and means for producing data of the image from the acquired MR raw data.

26. A method of MR imaging providing an of a subject through scanning based on a pulse sequence including pulsed gradients applied to the subject in a phase-encoding, read-out, and slice directions set to the subject, comprising the steps of:

acquiring a plurality of sets of MR raw data by performing a plurality of scans on a region of interest to be imaged of the subject with the phase-encoding direction spatially changed for at least one scan selected from the plurality of scans;

reconstructing each of the plurality of sets of MR raw data into a set of image data in a real space; and synthesizing the plurality of sets of reconstructed image data into data of the image.

27. The method of claim 26, wherein the synthesizing step performs at least one of addition processing and maximum intensity projection processing on the plurality of sets of reconstructed image data so as to produce the data of the image.

28. The method of claim 26, wherein the acquiring step includes setting the region of interest to be imaged to a single two-dimensional slice by controlling the pulsed gradient applied in the slice direction.

29. The method of claim 26, wherein the acquiring step includes setting the region of interest to be imaged to a multi-sliced region comprising a plurality of two-dimensional slices by controlling the pulsed gradient applied in the slice direction.

30. The method of claim 26, wherein the acquiring step includes setting the region of interest to be imaged to a three-dimensional volume by controlling the pulsed gradient applied in the slice direction.

31. An MRI system for providing an image of a subject placed in a static magnetic field by scanning, based on a pulse sequence including pulsed gradients applied in a phase-encoding, read-out, and slice directions set to the subject and an RF pulse applied to the subject, comprising:

a gradient coil for generating pulsed gradients in response to a pulsed current;

a gradient power supply connected to the gradient coil supplying the pulsed current to said gradient coil in response to information associated with the pulsed gradient included in the pulse sequence;

an RF transmitting/receiving system for transmitting to the subject an RF field corresponding to the RF pulse and receiving an MR signal from the subject;

a unit for producing data of the image from the MR signals; and a sequencer and controller for cooperatively performing the pulse sequence to acquire, through the RF transmitting/receiving system, the gradient coil, and the gradient power supply, a plurality of sets of MR raw data by performing a plurality of scans on a region of the subject of interest to be imaged, the phase-encoding direction for at least on scan selected from the plurality of scans being spatially changed with respect to the other plurality of scans.

32. The system of claim 31, wherein the producing unit comprises an element for reconstructing each of the plurality of sets of MR raw data into a set of image data in a real space, and an element for synthesizing the plurality of sets reconstructed image data into the data of the image.

33. The system of claim 32, wherein the synthesizing element performs at least one of addition processing and maximum intensity projection processing to the plurality of sets reconstructed image data to produce the data of the image.

34. The system of claim 32, wherein the controller includes an element that spatially changes the phase-encoding direction scan by scan into each of predetermined different directions.

35. The system of claim 32, wherein the controller includes an element that spatially changes the phase-encoding direction for a certain plurality of scans.

* * * * *